US012136220B2

(12) United States Patent
Vasilev et al.

(10) Patent No.: US 12,136,220 B2
(45) Date of Patent: Nov. 5, 2024

(54) METHOD AND SYSTEM FOR PROVIDING AN AT LEAST 3-DIMENSIONAL MEDICAL IMAGE SEGMENTATION OF A STRUCTURE OF AN INTERNAL ORGAN

(71) Applicant: LARALAB GmbH, Munich (DE)

(72) Inventors: Aleksei Vasilev, Munich (DE); Julian Praceus, Munich (DE)

(73) Assignee: Laralab GmbH, Munich (DE)

( * ) Notice: Subject to any disclaimer, the term of this patent is extended or adjusted under 35 U.S.C. 154(b) by 558 days.

(21) Appl. No.: 17/298,090

(22) PCT Filed: Dec. 2, 2019

(86) PCT No.: PCT/EP2019/083364
§ 371 (c)(1),
(2) Date: May 28, 2021

(87) PCT Pub. No.: WO2020/109630
PCT Pub. Date: Jun. 4, 2020

(65) Prior Publication Data
US 2022/0028085 A1   Jan. 27, 2022

(30) Foreign Application Priority Data
Nov. 30, 2018   (EP) .................................... 18209550

(51) Int. Cl.
G06T 7/11        (2017.01)
G06N 3/08        (2023.01)
G16H 30/40       (2018.01)

(52) U.S. Cl.
CPC ................. G06T 7/11 (2017.01); G06N 3/08 (2013.01); G16H 30/40 (2018.01);
(Continued)

(58) Field of Classification Search
CPC .......... G06T 2207/30048; G06T 7/0012; G06T 7/11; G06T 2207/30104; G06T 2200/04;
(Continued)

(56) References Cited

U.S. PATENT DOCUMENTS 7,860,283 B2 * 12/2010  Begelman ................. G06T 7/11
                                                  600/407
9,968,257 B1   5/2018  Burt
(Continued)

FOREIGN PATENT DOCUMENTS

JP         5731882 B2 *  6/2015
WO    WO-2016207875 A1 * 12/2016 ......... G06K 9/00442
WO    WO-2017091833 A1 *  6/2017 ......... G01R 33/5608

OTHER PUBLICATIONS

Tatsugami, F., et al. "Reduction of the total injection volume of contrast material with a short injection duration in 64-detector row CT coronary angiography." The British journal of radiology 83.985 (2010): 35-39. (Year: 2010).*
(Continued)

Primary Examiner — Aaron W Carter
Assistant Examiner — Courtney Joan Nelson
(74) Attorney, Agent, or Firm — Maginot, Moore & Beck, LLP

(57) ABSTRACT

The present invention provides a system and a computer-implemented method for generating at least one 4-dimensional medical image segmentation for at least one structure of a human heart. The method includes the steps of: providing a first 4-dimensional medical image comprising the at least one structure of the human heart, the medical image being based on a computed tomography scan image; generating a segmentation of at least part of the provided first 4-dimensional medical image using at least one first trained artificial neural network, wherein the at least one first trained artificial neural network is configured as a convolutional
(Continued)

processing network with U-net architecture; and generating at least one 4-dimensional medical image segmentation for the at least one structure of the human heart based at least on the segmentation generated by the at least one first trained artificial neural network.

21 Claims, 8 Drawing Sheets

(52) U.S. Cl.
CPC .............. *G06T 2207/10076* (2013.01); *G06T 2207/10081* (2013.01); *G06T 2207/20084* (2013.01); *G06T 2207/30048* (2013.01)

(58) Field of Classification Search
CPC ......... G06T 2210/41; G06T 7/10; G06T 7/20; G06T 17/00; G06T 2211/404; G06T 2207/10016; G06T 2207/30004; G06T 7/0016; G06T 7/174; G06T 2207/10076; G06T 2200/08; G06T 2211/412; G06T 3/4046; G06T 7/00; G06T 7/251; G06T 15/00; G06T 2207/10081; G06T 2207/20084; A61B 5/0044; A61B 8/5223; A61B 2576/023; A61B 6/503; A61B 8/06; A61B 34/10; A61B 2034/104; A61B 8/065; A61B 5/0035; A61B 5/026; A61B 5/02028; A61B 8/0883; A61B 34/25; A61B 5/004; A61B 8/483; A61B 8/466; G06N 3/045; G06N 20/00; G06N 3/02; G06N 3/08; G16H 30/40; G16H 50/50; G16H 10/60; G16H 50/20; G16H 40/67; G16H 70/60

See application file for complete search history.

(56) References Cited

U.S. PATENT DOCUMENTS

2017/0109881 A1* 4/2017 Avendi ...................... G06T 7/11
2018/0259608 A1* 9/2018 Golden ............ G01R 33/56308

OTHER PUBLICATIONS

Machine translation of JP5731882B2 (Year: 2015).*
Mahendra Khened, Varghese Alex Kollerathu, Ganapathy Krishnamurthi, Fully convolutional multi-scale residual DenseNets for cardiac segmentation and automated cardiac diagnosis using ensemble of classifiers, Medical Image Analysis, vol. 51, Published online Oct. 19, 2018, pp. 21-45, (Year: 2018). ISSN 1361-8415, https://doi.org/10.1016/j.media.2018.10.004. (https://www.sciencedirect.com/science/article/pii/S136184151830848X) (Year: 2018).*
Chengjia Wang et al: "A two-stage 3D Unet framework for multi-class segmentation on full resolution image", arxiv.org, Cornell University Library, 201 OLIN Library Cornell University Ithaca, NY 14853, Apr. 12, 2018 (Apr. 12, 2018), XP080870068, (Year: 2018).*
International Search Report corresponding to international application No. PCT/EP2019/083364, mailed Jan. 14, 2020 (18 pages).
Wang, Chengjia, et al., "A two-stage 3D Unet framework for multi-class segmentation on full resolution image," BHF Centre of Cardiovascular Science and MICCAI 2017 Multi-Modality Whole Heart Segmentation (MM-WHS) challenge. (10 pages).
Khened, Mahendra, et al., "Fully convolutional multi-scale residual DenseNets for cardiac segmentation and automated cardiac diagnosis using ensemble of classifiers," Medial Image Analysis 51 (2019) pp. 21-45. (26 pages).
Patravali, Jay, et al., "2D-3D Fully Convolutional Neural Networks for Cardiac MR Segmentation," Springer International Publishing AG, part of Springer Nature 2018 (10 pages).
"An Exploration of 2D and 3D Deep Learning Techniques for Cardiac MR Image Segmentation, " (8 pages).
Zoph, Barret and Quoc V. Le, "Neural Architecture Search with Reinforcement Learning," Google Brain (barretzoph, qvl@google.com. (16 pages).
Baker, Bowen, et al., "Designing Neural Network Architectures using Reinforcement Learning," Published as a conference paper at ICLR 2017. (18 pages).
Chen, Liang-Chieh, et al., Semantic Image Segmentation with Deep Convolutional Nets and Fully Connected CRF's, Published as a Conference paper at ICLR 2015. ( 14 pages).
Huang, Gao, et al., "Densely Connected Convolutional Networks," (9 pages).
Cicek, Ozgun, et al., "3D U-Net: Learning Dense Volumetric Segmentation from Sparse Annotation," ( 8 pages).
Bergmann, Paul, et al., "Improving Unsupervised Defect Segmentation by Applying Structural Similarity to Autoencoders,"(8 pages).
Jegou, Simon, et al., "The One Hundred Layers Tiramisu: Fully Convolutional DenseNets for Semantic Segmentation," ( 9 pages).
Sudre, Carole H., et al., "Generalised Dice Overlap as a Deep Learning Loss Function for Highly Unbalanced Segmentations," (8 pages).
Kayahbay, Baris, et al., "CNN-Based Segmentation of Medical Imaging Data," (24 pages).

* cited by examiner

METHOD AND SYSTEM FOR PROVIDING AN AT LEAST 3-DIMENSIONAL MEDICAL IMAGE SEGMENTATION OF A STRUCTURE OF AN INTERNAL ORGAN

This application is a 35 U.S.C. § 371 National Stage Application of PCT/EP2019/083364, filed on Dec. 2, 2019, which claims the benefit of priority to Serial No. EP 18209550.5, filed on Nov. 30, 2018, in the EPO, the disclosures of which are incorporated herein by reference in their entirety.

FIELD OF THE INVENTION

The present invention pertains to methods and systems for providing a 3-dimensional or 4-dimensional medical image segmentation for at least one structure of an internal organ, preferably a structure of the human heart, such as at least one heart valve and/or at least one structure anatomically adjacent and/or functionally related to at least one heart valve.

Although applicable for any kind of internal organ, the present invention and the corresponding underlying problems will be explained especially in detail in conjunction with a human heart. The human heart is an internal organ with a large time dependence due to its significant deformations over the cardiac cycle.

BACKGROUND OF THE INVENTION

In modern medicine, medical imaging techniques play an important role. In particular, computed tomography (CT), especially multi-slice CT, or magnetic resonance (MR) images, acquired with or without a contrast agent, provide ever more detailed and accurate images of internal organs and/or their internal structures.

However, distinguishing the structures of the internal organs from each other is often a non-trivial task. Some medical image data may have poor resolution or poor contrast. Not always is it possible to re-do an exam or scan, for instance because the tolerance for radiation and/or contrast agent doses is limited for each patient. Moreover, many internal organs have many intricate internal details which extend in complex ways in three spatial dimensions. Even if a physician or medical technician is able to move, zoom, and rotate through 3-dimensional medical image data, the human brain has not evolved to process such kind of information directly.

It is therefore desired to have access to methods and systems that help to segment the acquired image data, i.e. to provide different labels associated with different structures of the internal organ.

Recently, some types of artificial neural networks have gathered interest as tools for segmenting image data, in particular in the specific context of segmenting traffic image data for application in the field of autonomous driving.

For example, the scientific publication by Jégou et al.: "The One Hundred Layers Tiramisu: Fully Convolutional DenseNets for Semantic Segmentation", arXiv: 1611.09326v3 of 31 Oct. 2017, hereafter cited as "Jégou et al.", describes approaches to segment two-dimensional traffic images by providing labels for such structures as "sky", "building", "pole", "road", "sidewalk", "vegetation", "sign", "fence", "car", "pedestrian", "cyclist" or "void".

The scientific publication by Huang et al.: "Densely Connected Convolutional Networks", arXiv:1608.06993v5 of 28 Jan. 2018, hereafter cited as "Huang et al.", describes the so-called "densely connected" networks, or "DenseNets", in detail. A dense block is a block with a plurality of layers, wherein the output of each of the plurality of layers is not only transmitted to the next layer in the feed-forward direction of the dense block but is also itself concatenated to the input and/or the output of the last layer of the dense block and, optionally, also of all intermediate layers of the dense block.

The scientific publication by Kayalibay et al.: "CNN-based Segmentation of Medical Imaging Data", arXiv: 1701.03056v2 of 25 Jul. 2017, describes the use of trained artificial neural networks with U-net-like architecture configured for the segmentation of imaging data from the central nervous system as well as the bones of the hand.

However, image segmentation techniques are very specific to not only the information content of images, but also to the dimensionality of images. 3-dimensional image segmentation adds considerable complexity to the task of image segmentation. Moreover, in contrast to traffic images and the like, medical images generally only provide grayscale values for their pixels or voxels so that structures are often difficult to separate by differences in contrast.

Yet again another layer of complexity is added when the output of the segmentation is not 2-dimensional or even 3-dimensional, but 4-dimensional.

SUMMARY OF THE INVENTION

It is therefore one object of the present invention to provide improved methods and systems for providing an at least 3-dimensional medical image segmentation of (or: for) at least one structure of an internal organ, in particular a mammalian internal organ, preferably a human internal organ, more preferably a human heart.

According to a first aspect, the present invention provides a computer-implemented method for generating at least one at least 3-dimensional medical image segmentation for at least one structure (or: portion) of an internal organ (preferably a human heart), comprising the steps of: providing a first n-dimensional medical image comprising the at least one structure (or: portion) of the internal organ, wherein n=3 or n=4, wherein the first n-dimensional medical image is preferably based on, or identical with, at least one original medical image;

generating a segmentation for at least part of the provided first n-dimensional medical image using at least one first trained artificial neural network, wherein the at least one first trained artificial neural network is configured as a convolutional processing network with U-net architecture, wherein each convolutional processing network with U-net architecture comprises:
  a down-sampling path comprising at least two processing blocks (or: processing convolutional blocks) and at least two down-sampling blocks;
  an up-sampling path comprising at least two processing blocks (or: processing convolutional blocks) and at least two up-sampling blocks;
  wherein the down-sampling path generates a direct input and/or an indirect input for the up-sampling path; and
  generating at least one at least 3-dimensional medical image segmentation for the at least one structure of the internal organ based at least on the segmentation generated by the at least one first trained artificial neural network.

In some embodiments, at least one original medical image is provided as the first n-dimensional medical image. In other embodiments, the at least one original medical image may be processed in order to provide the first n-dimensional medical image. The at least one original medical image may be of any dimension, e.g. at least one 3-dimensional medical image, and/or at least one 4-dimensional medical image. The at least one original medical image consists in some embodiments of at least one single-modality image, preferably a computed tomography (CT) scan image. For example, the at least one original medical image may consist in some embodiments of an ECG gated CT scan including 3-dimensional medical images for at least two, preferably five or more, time points within the cardiac cycle.

The provided first n-dimensional medical image may in particular be provided as a 3-dimensional or 4-dimensional voxel structure.

The wording "segmentation of an n-dimensional medical image" (or of at least part of it) emphasizes that the segmentation is derived from said medical image, whereas the wording "segmentation for an n-dimensional medical image" emphasizes that the segmentation is generated specifically for that medical image.

An at least 3-dimensional medical image segmentation should be understood to either consist of a 3-dimensional medical image segmentation, or to comprise a 3-dimensional medical image segmentation (3 spatial dimensions) for medical image data at each of a plurality of different effective time points, or a (time-dependent) segmentation of a 3-dimensional (3 spatial dimensions) video, wherein the latter two variants can be designated as 4-dimensional medical image segmentations. The temporal dimension of multi-dimensional medical images is usually made up of effective time points instead of real-world time points, as will be explained in the following.

Medical images, especially three-dimensional images, are generally produced not as a one-time snapshot of an organ, but in a series of "slices" which together make up one "scan". These slices are often acquired sequentially but on a timescale that is much shorter than timescales relating to anatomic activities such as muscle contraction, valve opening/closing and so on. Thus, one three-dimensional image of a particular organ is usually made of slices produced each at a different real time point but aggregated together such as to form the three-dimensional image of that particular organ at an effective time point, i.e. as a time point on a time scale relevant for a diagnostic or surgical task.

For example, a three-dimensional image of a human heart may be provided for (or: at) an effective time point of the cardiac cycle. The cardiac cycle can be expressed in the stages of 1) Isovolumic relaxation, 2a) Inflow—ventricular filling, 2b) Inflow—ventricular filling with atrial systole, 3) Isovolumic contraction and 4) Ejection, wherein stages 1), 2a) and 2b) are jointly designated as "systole" or "systolic phase", and wherein stages 3) and 4) are jointly designated as "diastole" or "diastolic phase".

An effective time point with regard to the cardiac cycle may thus be expressed in a time measurement unit (such as seconds or milliseconds) but may also be expressed in a measurement unit relative to the duration of the cardiac cycle, for example 10% (or 30%, or 50%, etc.) of (or: along) the cardiac cycle, starting at a defined starting point, for example the start of the systolic phase.

When a plurality of effective time points is mentioned with regard to a cardiac cycle (i.e. with regard to a heart valve), it is preferable that at least one effective time point of the plurality of effective time points is part of the systolic phase and that at least one other effective time point of the plurality of effective time points is part of the diastolic phase. This presents a user efficiently with a wide range of information about the complete cardiac cycle of a particular heart.

More preferably, at least one effective time point is an effective time point of maximum opening or maximum closure of the leaflets of a heart valve. Additionally or alternatively, at least one effective time point is at an extremal, or maximum, deformation of an annulus structure of a heart valve to be determined. The term annulus structure shall comprise in particular an anatomically distinct annulus tissue structure of the heart valve, or a portion of the human internal organ that is considered to be an annulus of the valve or that has or provides annulus-like properties for the valve.

For example, one effective time point of maximum deviation could be an effective time point of minimum circumference (e.g. of maximum contraction) of the annulus structure, and/or one effective time point of maximum deviation could be an effective time point of maximum circumference of the annulus structure (e.g. of being maximally stretched, or of being completely relaxed, depending on the anatomical properties of the annulus structure). Additionally or alternatively, at least one effective time point is an effective time point of an extremal volume of a heart chamber, e.g. a minimum or a maximum volume of a heart chamber, corresponding to a maximum and minimum contraction, respectively.

For internal organs other than the heart, cycles or time frames other than the cardiac cycle may be relevant.

In the present context, "segmentation of at least part of the provided first n-dimensional medical image" means that, for at least a portion (or: part) of the medical image, labels are provided which indicate that this particular portion has specific properties and/or belongs to a specific anatomic structure (and/or belongs to a specific anatomic region of the internal organ). Such specific properties comprise, for example, physical properties such as elasticity, medical properties such as being especially sensible or as being critical and so on. Labels indicating belonging to a specific anatomic structure may comprise, for example when the human organ is a human heart (optionally including at least one blood vessel for transporting blood to or from the heart) indicating belonging to a particular portion or anatomical structure of the human heart, for example: indicating belonging to a particular heart chamber (a particular ventricle and/or a particular atrium), a particular blood vessel, a particular node and/or to any other particular anatomic region of the heart.

The labels may be integrated into the image data structure of the medical image itself, i.e. as a parameter value provided for individual voxels of the medical image, or the labels may be provided separately as a list or look-up table or the like.

The segmentation may also comprise labels (or, in other words: be realized by labels) that are implemented as a plurality of masks for the at least one effective time point, wherein each mask corresponds to a specific structure or portion of the human organ. For example, masks may be defined for a voxel structure (as one type of medical image) and have values of TRUE and FALSE for each voxel of the voxel structure, wherein a value of TRUE for a voxel indicates that said voxel belongs to the specific structure or portion to which the mask corresponds and a value of FALSE for a voxel indicates that said voxel does not belong to the specific structure or portion to which the mask corresponds. As a specific example, a mask for a left atrium (or right atrium) and a mask for a left ventricle (or right ventricle) may be defined. These masks, together with the voxel structure then form one possible type of a segmented digital representation. The same applies for pixels instead of voxels. Instead of values of TRUE or FALSE, masks may also have values that indicate for each pixel, or voxel, a probability that the voxel belongs to the specific structure or portion to which the mask corresponds.

The term in "segmented digital representation" herein refers to a combination of a medical image and at least one type of corresponding label or, in other words, to a combination of a medical image and its corresponding medical image segmentation.

The medical image segmentation may be a complete segmentation or an at least partial segmentation. The term "at least partial segmentation" comprises the case where every structure in the at least part (or: portion) to be segmented of the medical image is provided with a label (complete segmentation) but also comprises the case (partial segmentation) where only a single structure in the at least part (or: portion) to be segmented of the medical image is provided with a label (e.g. a single mask) and further comprises the case (partial segmentation) where a sub-set of the total set of structures of the medical image is provided with corresponding labels.

The medical image segmentation may also comprise labels (or: be realized by labels) that are implemented as a plurality of outer contours for the at least one effective time point, wherein each outer contour corresponds to the outer contour of a specific structure of the human organ. An outer contour may be represented by a polygon mesh defined by a collection of vertices, edges and/or faces. These outer contours may be calculated from another type of label, using for example a marching cubes algorithm.

The term "medical image segmentation based on the first n-dimensional medical image" is supposed to be understood such that the labels may be provided for the first n-dimensional medical image itself (in that case the segmentation may be designated as a segmentation for the first n-dimensional medical image), or that labels may be provided for a re-scaled n-dimensional medical image that itself is based on the first n-dimensional medical image.

Any labels that are generated for the first n-dimensional medical image may in an optional step be adapted (in particular, re-sized and/or positioned) to fit the at least one original medical image. A physician may then view the at least one original medical image together with the labels to perform an assisted diagnosis or to plan an intervention. The generated medical image segmentation may thus also be a combination of the at least one original medical image and the labels generated by the first trained artificial neural network, optionally after a corresponding re-scaling, and/or re-positioning of either or both.

Preferably, in the first trained artificial neural network each up-sampling or down-sampling block is followed by a processing block (or: processing convolutional block) such that the results of the up-sampling or down-sampling, respectively, can be processed immediately, making use of the re-sampled format of the latent representation.

Preferably, the first trained artificial neural network comprises as many up-sampling blocks as it comprises down-sampling blocks.

The term "direct input" shall be understood to mean that the output at the end of the down-sampling path is used as input at the beginning of the up-sampling path. "Indirect input" shall be understood to mean that therebetween additional elements, e.g. an additional processing (convolutional) block, may be arranged. Then, the output at the end of the down-sampling path may be used as input to the additional element, and the output at the end of the additional element may be used as the input at the beginning of the up-sampling path.

The first n-dimensional medical image, or at least one original medical image on which that first n-dimensional medical image is based (or: is generated from), may e.g. be a computed tomography scan (CT scan) produced without contrast agent ("non-contrast CT scan") or a CT scan produced with a total dose of less than 50 ml of contrast agent, preferably less than 30 ml, more preferably less than 20 ml ("ultra-low contrast CT"). Such scans are usually less stressful for the body of a patient but produce less contrasts between shades of gray. For the human eye and mind and for currently available computer implemented image segmentation methods shapes in such a CT scan produced without contrast agent may be effectively indistinguishable because the human visual processing only is able, or respectively available computer implemented methods only are able, to process visual differences with a certain minimum contrast. The methods and systems of the present invention on the other hand make it possible to generate an at least 3-dimensional medical image segmentation even from such images. That segmentation may then be used, for example, for planning and/or guidance of transcatheter heart interventions.

Generating 4-dimensional medical image segmentations has the advantage that some structures (such as the bases of some leaflets of some heart valves, commissures, anomalies of heart valves and/or the like) may only be visible at certain effective time points. Generating 4-dimensional medical image segmentations thus enables a physician, medical technician or implant manufacturer to examine the human organ in question completely.

Moreover, for some interventions, dynamic (4-dimensional) views or overlays of medical image segmentations (and/or planning models which derive from the medical image segmentations) over medical image data from a different source and acquired in real time (e.g. two-dimensional fluoroscopy images) may be especially helpful, for example with transcatheter heart interventions (repair, replacement), in particular regarding the mitral valve and the tricuspid valve. To show such overlays of segmentations (and/or planning models which derive from the segmentations), a registration between coordinate systems of the medical image segmentations and the medical image data from the different source may be performed.

Another advantage of the method is that accurate and robust segmentations can be provided for structures (or portions) which have a great variability in terms of their anatomical morphology (e.g. the left atrial appendage and/or abnormal heart chambers due to e.g. heart valve diseases and/or leaflets of a heart valve) and for structures (or portions) that are not or almost not shown in the provided medical image by visible differences in contrast.

The invention further allows to segment dynamic (e.g. moving and/or changing shape) structures, that are not separable from other structures and/or not visible, due to visible differences in contrast in a 3-dimensional medical image, by taking into account information from a 4-dimensional medical image and thus the dynamic of the structure. For example, a Right Coronary Artery is often not or only part-wise separable from surrounding structures (e.g. from the Right Atrium or Right Ventricle), or in another example leaflets of an atrioventricular heart valve are often only rudimentarily visible in a 3-dimensional CT image (even with contrast agent), but the invention provides a method/system that is able to segment the Right Coronary Artery or such leaflets automatically and more accurately for each 3-dimensional CT image as any currently known method in the state of the art, by taking into account multiple, at least two, 3-dimensional CT images, where each 3-dimensional CT image represents a different stage of the cardiac cycle of the same patient, and thus the dynamic of the Right Coronary Artery or the leaflets of the valve respectively.

The invention also provides, according to a second aspect, a system for generating at least one at least 3-dimensional medical image segmentation for at least one structure of an internal organ (preferably a human heart), comprising:
a computing device configured to implement:
an input module configured to provide a first n-dimensional medical image of the at least one structure of the internal organ, wherein n=3 or n=4, wherein the first n-dimensional medical image is preferably based on, or identical with, at least one original medical image; and
a controller implementing a first trained artificial neural network, wherein the trained artificial neural network is configured as a convolutional processing network with U-net architecture,
wherein each convolutional processing network with U-net architecture comprises:
a down-sampling path comprising at least two processing convolutional blocks and at least two down-sampling blocks;
an up-sampling path comprising at least two processing convolutional blocks and at least two up-sampling blocks;
wherein the down-sampling path generates a direct or an indirect input for the up-sampling path;
wherein the first trained artificial neural network is trained and configured to generate a segmentation of at least part of the provided first n-dimensional medical image; and
an output module configured to generate at least one at least 3-dimensional medical image segmentation based at least on the segmentation generated by the at least one first trained artificial neural network.

The computing device may be realized as any device, or any means, for computing, in particular for executing a software, an app, or an algorithm. For example, the computing device may comprise a central processing unit (CPU) or processor, an input interface, an output interface and a memory operatively connected to the CPU. The computing device may also comprise an array of CPUs, an array of graphical processing units (GPUs), at least one application-specific integrated circuit (ASIC), at least one field-programmable gate array, or any combination of the foregoing.

Some, or even all, modules of the system may be implemented by a cloud computing platform. The computing device may be configured as a cloud computing platform or a remote server which is operatively remotely connected to a graphical user interface (GUI) configured to display information to a user and to receive user input from the user. For example, the GUI may be run on a local machine in a hospital environment while at least some of the computing power is provided by a remotely connected server or cloud computing platform.

The system may comprise, or be operatively coupled to, or be integrated into, a system for processing the generated at least one at least 3-dimensional medical image segmentation (optionally together with a corresponding n-dimensional medical image).

For example, the system for processing may automatically determine, or assist a user in determining, a digital representation of a heart valve, more specifically an annulus or annulus structure, leaflets and/or commissures of the heart valve, within the first n-dimensional medical image and/or within the at least one at least 3-dimensional medical image segmentation.

Said annulus structure can be determined as an outer contour line (or: border line) between different structures (i.e. differently labelled structures), e.g. between two adjacent heart chambers, such as between left ventricle and left atrium, or as between right ventricle and right atrium of a human heart. The annulus structure may also be a directly segmented volume (such as a tube), i.e. a structure that has its own label. The annulus structure may also be determined based on segmented leaflets (e.g. based on the outer contour of such leaflets).

The determined digital representation of the heart valve, annulus or annulus structure, leaflets and/or commissures of the heart valve may then be used, automatically or on the user's command, as a further input (into the input layer and/or into a hidden layer) for at least one of the artificial neural networks described with respect to the present invention in order to improve its output (i.e. the segmentation generated by it). In particular, it may be used, with or without being re-scaled first, depending on the case at hand, as a further input into the input layer and/or into a hidden layer of one (or multiple, or all) of the at least one first trained artificial neural network.

For example the outer contour line (or: border line) between the tissue of two adjacent heart chambers may be determined based on a user input, and may then be used as a separation between labels for the two adjacent heart chambers. One application for this is that the outer contour line (or: border line) may be reviewed and/or adjusted by a skilled physician or medical technician so that this information is considered to be superior to the automatically generated medical image segmentation. The reviewed and/or adjusted outer contour line (or: border line) can then be used to provide an improved medical image segmentation when it is used as a further input into a trained artificial neural network as described above, or can be used in or as training data for training the artificial neural network, e.g. the at least one first artificial neural network.

According to a third aspect, the invention provides a non-transitory computer-readable data storage medium comprising executable program code configured to, when executed, perform a method according to an embodiment of the first aspect. The data storage medium may consist of, or comprise, a CD-ROM, a memory stick, a USB stick, a hard drive, a solid-state data storage device, a DVD, a BluRay-disc, an/or the like.

According to a fourth aspect, the invention provides a computer program product comprising executable program code configured to, when executed, perform a method according to an embodiment of the first aspect.

According to a fifth aspect, the invention provides a data stream comprising, or configured to generate, executable program code configured to, when executed, perform a method according to an embodiment of the first aspect.

According to a sixth aspect, the invention provides a method for training, in particular supervised or semi-supervised training of, an artificial neural network for use in a method according to an embodiment of the first aspect and/or for use in a system according to an embodiment of the second aspect. In the training, preferably a dice loss function or a generalized dice loss function as described e.g. by Sudre et al., "Generalised Dice overlap as a deep learning loss function for highly unbalanced segmentations", arXiv: 1707.03237v3 of 14 Jul. 2017 is used. The training data preferably comprises ground truth data that has been approved by a medical expert. Available training data may be automatically augmented by any or all of the following operations:
- at least one spatial rotation;
- at least one re-scaling operation (e.g. in the same way as optionally applied to the medical image);
- at least one shear transformation;
- noise addition.

In some advantageous embodiments, the training data set is augmented with slight rotations (f. e. by a random degree alpha, where −30<alpha<30, along a randomly selected axis) and/or small Gaussian noise addition and/or slight random sheer transformations and/or scaling along a random axis. Data augmentation helps the artificial neural network to be trained to be robust to different possible variations in the anatomical structures.

Further advantageous embodiments and variants are disclosed in the following, in particular in the dependent claims as well as in the drawings and the corresponding sections of the description.

In some advantageous embodiments, the method further comprises the steps of: providing a second n-dimensional medical image, with n=3 or n=4, preferably having the same dimensionality as the provided first n-dimensional medical image, wherein the second n-dimensional medical image is preferably based on, or identical with, at least one original medical image;
- generating a segmentation for (or: of) at least part of the second n-dimensional medical image using a second trained artificial neural network configured as a convolutional processing network with U-net architecture,
- determining a portion of the segmentation for the second n-dimensional medical image which comprises the at least one structure of the internal organ;
- extracting a portion of the provided second n-dimensional medical image (or of the at least one original medical image) corresponding to the determined portion of the segmentation for the second n-dimensional medical image;
- providing the extracted portion as the first n-dimensional medical image to the at least one first trained artificial neural network.

Extracting the portion of the provided second n-dimensional medical image may comprise, or consist of, determining a box comprising voxels (optionally for each of a plurality of effective time points) and providing that determined box as the first n-dimensional medical image.

Preferably, the second trained artificial neural network is configured with less complexity than the first trained artificial neural network. The second trained artificial neural network can thus be used to quickly, and at low computational resource cost, extract a portion of interest from the provided second n-dimensional medical image to be then processed by the at least one first trained artificial neural network.

Instead of (or in addition to) the second trained artificial neural network, also other approaches to determine a portion of the provided second n-dimensional medical image which comprises the at least one structure of the internal organ are possible based on which then the portion may be extracted and provided as the first n-dimensional medical image. For example, a region (or: box) of interest may be predicted directly from the second n-dimensional medical image, e.g. based on heuristic data where the at least one structure is usually arranged.

In some advantageous embodiments, the structure of the internal organ comprises at least one heart valve and/or annulus structure, at least one blood cavity, at least one muscle tissue structure, at least one implant and/or at least one anomaly.

In some advantageous embodiments, as the at least one at least 3-dimensional medical image segmentation, a 4-dimensional medical image segmentation is generated.

The first n-dimensional medical image may comprise a plurality of 3-dimensional medical images, each for (or: at) a different effective time point. A respective segmentation for (or: of) at least two (preferably five or more) of the plurality of 3-dimensional medical images may be independently (or: separately) generated by the at least one first trained artificial neural network. In other words, one segmentation for a first effective time point may be generated by a first instance of the first trained artificial neural network, and another segmentation for a second (third, fourth, fifth . . . ) effective time point may be generated by a second (third, fourth, fifth . . . ) instance of the (same) first trained artificial neural network. The generated 4-dimensional medical image segmentation may comprise at least two (preferably five or more) of the independently, or separately, generated segmentations for the plurality of 3-dimensional medical images.

In some advantageous embodiments the method further comprises: generating a 3-dimensional medical image segmentation corresponding to a first effective time point within the 4-dimensional medical image segmentation to be generated. At least one 3-dimensional medical image segmentation corresponding to at least one second effective time point within the 4-dimensional medical image segmentation to be generated may be generated by the at least one first trained artificial neural network based on the 3-dimensional medical image data for (corresponding to) the respective (second) effective time point and at least one output and/or at least one latent representation and/or at least one hidden feature generated by the at least one first trained artificial neural network when generating the 3-dimensional medical image segmentation corresponding to the first effective time point. For example, a latent representation within a first instance of a first trained artificial neural network processing a 3-dimensional medical image at a first effective time point may be used as an input into a hidden layer of at least one second instance of the first trained artificial neural network processing a 3-dimensional medical image at a second effective time point.

In this way, the knowledge gained by one of the instances of the first trained artificial neural network may be used in another instance of the same first trained artificial neural network processing data for another effective time point.

The term "output" of an artificial neural network should be understood to refer in particular to the features that are output by the output layer of the artificial neural network. Hidden features may refer to features, or channels, as output by a hidden layer of the artificial neural network. A latent representation (or: hidden state) may refer to the totality of outputs of a hidden layer of the artificial neural network.

In some advantageous embodiments, the at least one output and/or at least one latent representation and/or at least one hidden feature generated by the at least one first trained artificial neural network when generating the 3-dimensional medical image segmentation artificial corresponding to the first effective time point is used when generating 3-dimensional medical image segmentations for the at least one structure of the internal organ for a plurality of other effective time points that are adjacent to the first effective time point.

In some advantageous embodiments, the first and the second effective time point (and preferably all of the effective time points) correspond to different stages of a cardiac cycle.

In some embodiments, the generated 4-dimensional medical image segmentation may comprise labels for at least one leaflet of at least one heart valve. Such segmentations can be used, for example, to derive at least one morphologic property and/or a morphologic abnormality of the corresponding at least one leaflet and/or corresponding heart valve.

In some advantageous embodiments, at least one processing block in at least one of the trained artificial neural networks (e.g. at least one first and/or second trained artificial neural network) comprises a plurality of convolutional filter layers, wherein at least two of the plurality of convolutional filter layers apply different strides.

In some advantageous embodiments, each processing block comprises a plurality of convolutional filter layers with 3-dimensional convolutional kernels, wherein optionally at least two of the plurality of convolutional filter layers may apply different strides. 3-dimensional (3 spatial dimensions) convolutional filters are able to better understand (or: process) complex 3-dimensional shapes of structures of internal organs within 3-dimensional (3 spatial dimensions) medical images.

In some advantageous embodiments, at least one processing block in at least one of the trained artificial neural networks comprises a bottleneck structure in which an r×r×r 3-dimensional convolution layer follows an q×q×q 3-dimensional convolution layer with reduced number of the output channels compared to the number of the input channels, wherein r and q are integers and wherein q is smaller than r.

In some advantageous embodiments, at least one of the processing blocks in at least one of the trained artificial neural network comprises at least one convolutional capsule layer.

Herein, at least one convolutional capsule layer consists of at least one capsule comprising a group of neurons whose output represents an entity or an entity part including its variants (position, size, orientation, deformation, etc.). If the layer of the artificial neural network preceding the at least one capsule layer is not a capsule layer itself, the input to the at least one capsule layer is generated by grouping the features of the output of the preceding layer into the capsules. If the layer of the artificial neural network preceding the at least one capsule layer is also a capsule layer, the output of the preceding capsule layer is directly used as the input to the following capsule layer. The output of the at least one capsule layer is generated by transforming its input into votes for the at least one capsule layer capsules via learned transformations (e.g. via learned linear transformations) and calculating the output of the capsule layer based on the votes during a routing procedure which may comprise a fuzzy clustering algorithm applied within a convolutional kernel.

Convolutional capsule layers have been proposed by Geoffrey Hinton et al., for example in "Geoffrey Hinton, Sara Sabour, and Nicholas Frosst. Matrix capsules with em routing. 2018", hereafter cited as "Hinton et al.". Therein, "em" stands for "expectation maximisation". Dynamic routing as an alternative to the em routing procedure described in "Hinton et al." has been proposed in: "Sara Sabour, Nicholas Frosst, and Geoffrey E Hinton. Dynamic routing between capsules. In: Advances in Neural Information Processing Systems 30, pages 3856-3866. Curran Associates, Inc., 2017", hereafter cited as "Sabour et al.". In the scientific publication "Dilin Wang and Qiang Liu. An optimization view on dynamic routing between capsules, 2018", an optimized dynamic routing procedure is described. A procedure called "spectral routing" is proposed in the scientific publication "Mohammad Taha Bahadori. Spectral capsule networks. 2018". The so-called Learning Vector Quantization, LVQ, routing is proposed in "Thomas Villmann and Frank-Michael Schleif, editors. Machine Learning Reports 02/2018, volume 1 of Machine Learning Reports, 2018. ISSN:1865-3960 http://www.techfak.uni-bielefeld.de/ "fschleif/mlr/mlr02 2018.pdf." Another routing procedure is described in the scientific publication "Capsule Routing via Variational Bayes. 2019", available e.g. at https://arxiv.org/pdf/1905.1145.pdf. A new approach to group neural network features in capsules is proposed in "Adam R. Kosiorek and Sara Sabour and Yee Whye Teh and Geoffrey E. Hinton. Stacked Capsule Autoencoders", available e.g. at https://arxiv.org/pdf/1906.06818.pdf.

For the present invention, any known routing procedure for capsule layers, i.e. em routing, dynamic routing, optimized dynamic routing, spectral routing, LVQ routing or routing via variational Bayes and so on or any other known way of introducing capsules into the neural network, e.g. stacked capsule autoencoders, may be used.

Capsule layers endow artificial neural networks with several useful features:
  Approximate equivariance under transformations of entity properties
  Robustness to adversarial attacks
  Explicit learning of part-whole relationships between network layers All together, these features allow the artificial neural network to generalise better to unseen variants of the input data and thus to yield better segmentation results in terms of the accuracy.

Therefore, capsule layers are well suited for capturing or determining information about structures with a high morphological variability and/or dynamic structures, for example leaflets of heart valves moving during the cardiac cycle.

Down-sampling in the down-sampling blocks is preferably done by 3-dimensional maxpooling, preferably with the same stride and the same kernel size for each of the three spatial dimensions. For this reason, it may be beneficial to re-scale the provided first and/or second n-dimensional medical image such that the distances between the pixels (or voxels) are the same for all three spatial dimensions.

In some advantageous embodiments, at least one up-sampling block in at least one of the trained artificial neural networks (e.g. at least one first and/or second trained artificial neural network) applies a nearest neighbour and/or trilinear interpolation method. An up-sampling block that applies a nearest neighbour and/or trilinear interpolation method has the advantage that it does not introduce additional learnable parameters in the network, reducing the network size and preventing it from overfitting.

Additionally or alternatively, at least one up-sampling block may comprise at least one transpose convolutional layer.

In some advantageous embodiments, a 3-dimensional medical image (in particular the first and/or second medical image or part of the first and/or second medical image) is generated from a multi-slice original medical image by generating 3-dimensional voxels taking into account the values of the pixels of slices of the multi-slice medical image as well as distances between the pixels and distances between the slices. The distances are preferably defined in relation to actual distances and dimensions of the internal organ.

In some advantageous embodiments, the method further comprises the steps of:
providing a third trained artificial neural network configured as an autoencoder or variational autoencoder;
inputting the at least part of the provided first n-dimensional medical image (i.e. that data that is also input into the at least one first trained artificial neural network) into the third trained artificial neural network; and
outputting, based on an output of the third trained artificial neural network, an output signal indicating a quality confidence score of the segmentation generated by the at least one first trained artificial neural network and/or indicating an anomaly. When the output signal indicates an anomaly, that information may be used by the first trained artificial neural network to segment (i.e. to provide a label of the segmentation for) also that anomaly within the provided first n-dimensional medical image.

Preferably, the output signal is based on the output of the third trained artificial neural network and the input of the third trained artificial neural network, in particular based on a difference between said output and said input.

The third trained artificial neural network may be implemented by a computing device which may also be configured to generate the output signal based on the output of the third trained artificial neural network, preferably based on the output of the third trained artificial neural network and the input of the third trained artificial neural network, in particular based on a difference between said output and said input.

The output signal may e.g. provide, or be used as a basis for, an automatic evaluation if the generated medical image segmentation is acceptable or not and/or should be provided to a user for review and/or verification. The output signal may also be, or be used as a basis for, a signal for the user suggesting to the user to in particular review one structure, or one label of the generated medical image segmentation.

In some advantageous embodiments, a plurality of first trained artificial neural networks which are differently configured and/or differently trained is provided. At least two of the plurality of the first trained artificial neural networks may be configured as a respective convolutional processing network with U-net architecture. A respective candidate segmentation of at least part of the provided first n-dimensional medical image may be generated by each of the plurality of provided first trained artificial neural networks. The at least 3-dimensional medical image segmentation may be generated based on the generated candidate segmentations, e.g. on an average of the generated candidate segmentations or the like.

In this way, for each task the most efficient or most suited of the plurality of first trained artificial neural network may be employed.

In some advantageous embodiments, a regularization term taking into account anatomical information is added to the artificial neural network loss function of any of the first and/or second trained artificial neural networks as described herein, in particular of the first artificial neural network. The regularization term may be computed as a generalized dice loss and/or average voxel-wise Euclidean distance between down-sampled ground truth labels and some latent representations of the network followed by 1×1×1 convolutional layers with p+1 output channels, where p is the number of segmented structures.

The regularization term may also be learned with an adversarial training, where another artificial neural network is trained to extract the structural difference between the ground truth labels and the labels produced by the respective first and/or second trained artificial neural network. The regularization term may also be computed as a generalized dice loss and/or average voxel-wise Euclidean distance between the ground truth labels and the labels produced by the respective trained artificial neural network, with both of them post-processed by the encoder branch of a pre-trained (on the ground truth labels) autoencoder or variational autoencoder. All of the regularization terms mentioned above incorporate structural information and inter-structure dependencies into the original loss function which is not aware of these properties itself.

BRIEF DESCRIPTION OF THE DRAWINGS

The invention will be explained in greater detail with reference to exemplary embodiments depicted in the drawings as appended.

The accompanying drawings are included to provide a further understanding of the present invention and are incorporated in and constitute a part of this specification. The drawings illustrate the embodiments of the present invention and together with the description serve to explain the principles of the invention. Other embodiments of the present invention and many of the intended advantages of the present invention will be readily appreciated as they become better understood by reference to the following detailed description. The elements of the drawings are not necessarily to scale relative to each other. Like reference numerals designate corresponding similar parts.

Figure 1:
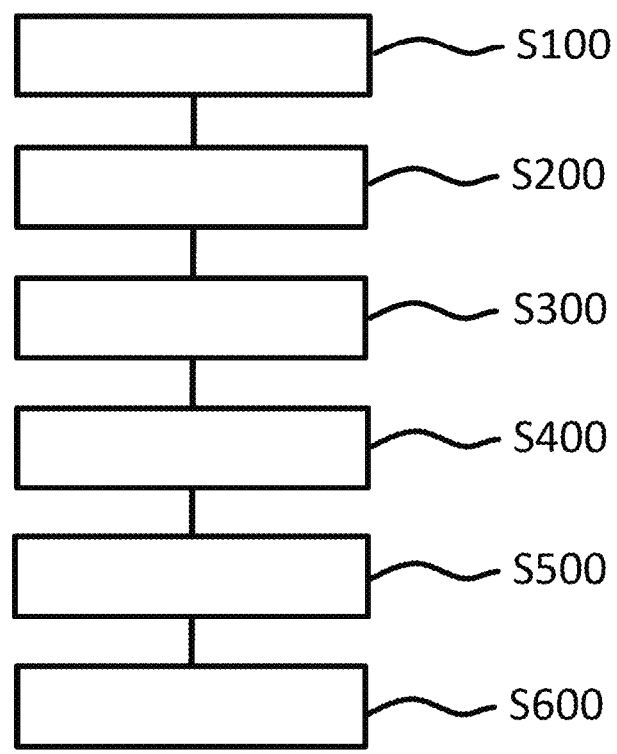
FIG. 1 shows a schematic flow diagram illustrating a method for generating a 4-dimensional medical image segmentation for at least one structure of an internal organ according to an embodiment of the first aspect of the invention.

In the figures, like reference numerals denote like or functionally like components, unless indicated otherwise. Any directional terminology like "top", "bottom", "left", "right", "above", "below", "horizontal", "vertical", "back", "front", and similar terms are merely used for explanatory purposes and are not intended to delimit the embodiments to the specific arrangements as shown in the drawings. The numbering of method steps primarily serves for designating the method steps and shall not be considered as restricting the method to be necessarily performed in the exact order according to the steps, if not explicitly or implicitly described otherwise.

DETAILED DESCRIPTION OF THE INVENTION

Although specific embodiments have been illustrated and described herein, it will be appreciated by those of ordinary skill in the art that a variety of alternate and/or equivalent implementations may be substituted for the specific embodiments shown and described without departing from the scope of the present invention. Generally, this application is intended to cover any adaptations or variations of the specific embodiments discussed herein.

FIG. 1 shows a schematic flow diagram illustrating a method for generating a 4-dimensional medical image segmentation for at least one structure of an internal organ according to an embodiment of the first aspect of the invention.

Figure 2:
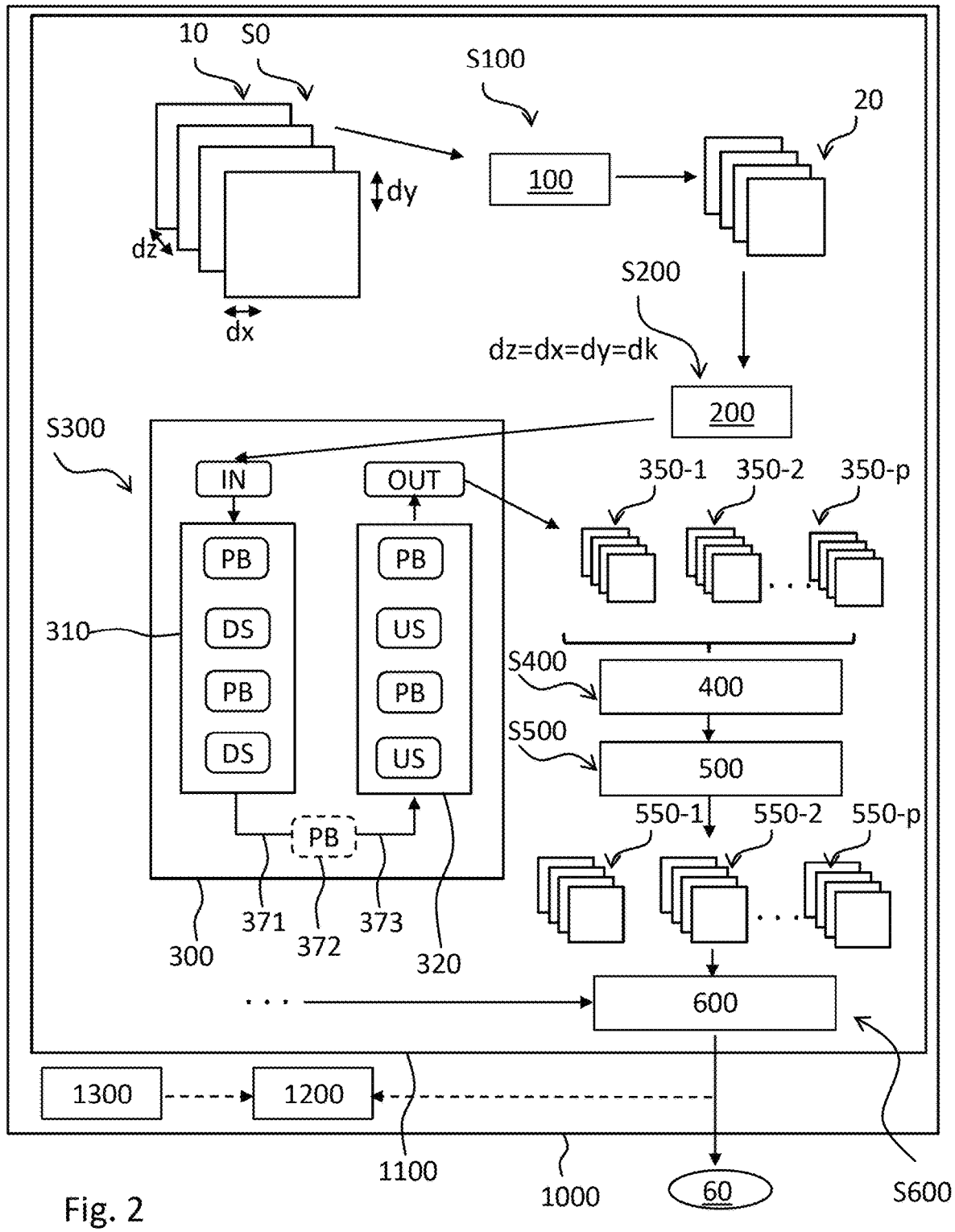
FIG. 2 shows a schematic block diagram illustrating a system for generating a 4-dimensional medical image segmentation for at least one structure of an internal organ according to an embodiment of the second aspect of the invention.

In describing the method according to FIG. 1, reference will also be made to FIG. 2 and the reference signs shown therein to better illustrate the present invention.

FIG. 2 shows a schematic block diagram for illustrating a system 1000 for generating a 4-dimensional medical image segmentation for at least one structure of an internal organ according to an embodiment of the second aspect of the invention. The system 1000 according to FIG. 2 is preferably configured to perform the method according to an embodiment of the first aspect of the present invention, in particular to perform the method described with respect to FIG. 1. Accordingly, the system 1000 may be adapted or modified according to any options, variants, or modifications described with respect to the method according to the first aspect, in particular with respect to the method of FIG. 1, and vice versa. Still, it should be understood that the method of FIG. 1 may be performed independently of the system 1000.

Referring to FIG. 1 and FIG. 2, in an optional step S0, at least one, preferably a plurality, of original medical images 10 is provided (e.g. a multi-slice scan image such as from a computed tomography). For example, step S0 may comprise receiving the at least one original medical image 10 from an interface, for example from a picture archiving and communication system (PACS) of a hospital, or directly from a medical imaging device, or the like.

In a step S100, a first n-dimensional medical image 20 comprising a structure of an internal organ is provided (or: generated), wherein n=3 or n=4, for example based on the at least one original medical image 10. The method may comprise several steps for providing (or: generating) the n-dimensional medical image 20 based on the at least one original medical image 10, as will be described with respect to FIG. 2 and FIG. 7 in the following.

However, providing the first n-dimensional medical image 20 may additionally or alternatively comprise, or consist of, receiving the n-dimensional medical image 20 from an interface, for example from a picture archiving and communication system (PACS) of a hospital, or directly from a medical imaging device, or the like.

As illustrated in FIG. 2, step S100 may be performed by an input module 100 (or input interface) of the system 1000. The system 1000 comprises a computing device 1100 that is configured to implement the input module 100 as well as any other modules described in the context of the system 1000. The computing device 1100 may be realized as any device, or any means, for computing, in particular for executing a software, an app, or an algorithm. In particular, the computing device 1100 may comprise a cloud computing platform such that any or all of the modules of the system 1000 may be executed by said cloud computing platform. Any or all of the modules described herein may be implemented by, or as, software.

In the example of FIG. 2, a plurality of original medical images 10 is provided, e.g. a plurality of 2-dimensional slices (such as from a series of planar CT scans), wherein the pixels within each slice have distances dx, dy from one another, and the slices have distance dz from one another. The distances dx, dy and dz extend in a x-direction, a y-direction and a z-direction, respectively, wherein the x-direction, the y-direction and the z-direction form an orthogonal spatial coordinates tripod. The (original) distances dx, dy, dz between the individual pixels (or voxels) of the plurality of original medical images 10 in the respective directions may be used to define a "size" for each pixel (or voxel). Distances between pixels (or voxels) shall be understood as distances between their respective coordinates in the orthogonal coordinates tripod.

As will be described in the following, from the plurality of original medical images 10 an n-dimensional voxel structure may be generated which may then be changed in a re-scaling operation so that the total number of pixels (or voxels) as well as the distances between resulting pixels (or voxels), distances defined with regard to the actual internal organ, are changed while the changed medical image still includes the same portion of the internal organ.

A user may be presented with a graphical user interface, GUI, by a display device (a computer screen, a touch screen or the like) operatively coupled to a computing device, and may be given the option to select one medical image out of a list of available medical images, e.g. from the PACS. The graphical user interface, GUI, may be implemented as a web interface run by a remote server or cloud computing platform as computing device, or it may be run by a local computing device present at the same location as the PACS.

In the present example, we will describe the case that a 4-dimensional medical image is provided (or: generated) in step S100 based on the plurality of original medical images 10, i.e. one 3-dimensional medical image for each of a plurality of effective time points is provided. Other variants will be described later herein. Moreover, we will describe the case that the 4-dimensional medical image comprises, or consists of, medical image data about at least a portion of a human heart.

In this case, the effective time points are advantageously designated as percentages of the cardiac cycle. In the following, percentages of the cardiac cycle will be given with respect to the start of the systolic phase as starting point; it should be understood that other starting points may be equivalently chosen. Preferably, the 4-dimensional medical image 10 comprises at least one 3-dimensional medical image for an effective time point during the systolic phase, for example of 30% of the cardiac cycle, and at least one 3-dimensional medical image for an effective time point during the diastolic phase, for example of 70% of the cardiac cycle.

In some advantageous variants, further 3-dimensional medical images for additional effective time points during the cardiac cycle are provided as part of the first 4-dimensional medical image 10, e.g. at 0%, 10%, 20%, 40%, 50%, 60%, 80%, and/or 90% of the cardiac cycle, 100% being effectively equal to 0%.

If the provided plurality of original medical images 10 comprise, for each effective time point, a plurality of two-dimensional slices (e.g. CT slices), then as part of step S100 a voxel structure for each effective time point may be automatically generated by extending pixels of size dx·dy (distances between pixels in the respective direction) into a third, orthogonal direction (or dimension) z such that the (then) voxels have size dx·dy·dz, wherein the size dz of the voxels in the third direction is given by the distance that lies between the two-dimensional slices. In multi-slice CT scans, the distance between the slices is a known parameter which may e.g. be automatically extracted from a DICOM file.

In the step S100, providing the first 4-dimensional medical image may optionally also comprises data normalization. For example, all pixel or voxel values may be divided by an average pixel or voxel value for the corresponding 3-dimensional medical image or by an average pixel or voxel value for the entire provided first 4-dimensional medical image. Alternatively, the average pixel or voxel value for the corresponding 3-dimensional medical image or for the entire provided first 4-dimensional medical image may be subtracted from all pixel or voxel values. The result may optionally be divided by a standard deviation, or such that the resulting pixel or voxel values all lie in the range from 0 to 1, both included. Such a data normalization step may, additionally or alternatively, performed at any time in the method as described herein and not only by, or as part of, the input module 100.

In an optional step S200, the provided first 4-dimensional medical image 20 is re-scaled (or resampled) in the spatial dimensions, in particular up-scaled or down-scaled, for example by using a convolution and/or deconvolutional layer of a re-scaling artificial neural network (e.g. with fixed weights) implemented by the computing device 1100, respectively. The result is a re-scaled version of the first 4-dimensional medical image 20.

Up-scaling (down-scaling) means that the resolution, i.e. amount of pixels or voxels in at least one spatial dimension is increased (decreased). Re-scaling the 4-dimensional medical image may, in particular, comprise re-scaling each of the 3-dimensional medical images of the 4-dimensional medical image with regard to at least one spatial dimension. Re-scaling may also be performed by nearest-neighbour interpolation, trilinear interpolation (i.e. linear interpolation in three dimensions) and/or the like. For different re-scaling operations, different methods may be used. For the down-scaling, nearest-neighbour interpolation is preferred.

Preferably, the voxels having distances dx, dy, dz between them in x-, y- and z-dimension, respectively, are re-scaled in step S200 so as to have a common distance dk in each of the three dimensions. In some embodiments or variants, dk may be fixed; in others, dk may be determined automatically. It is more preferred that dk is equal to or larger than the previous values dx, dy, dz such that in general a down-scaling is performed, and the resolution in a respective dimension (voxel/mm) is lowered. For example, dk may be set automatically to the largest of dx, dy and dz, or to the largest of dx, dy and dz multiplied with a predetermined factor larger than one.

As a specific example, in a given CT medical image slices may be set 2 mm apart from one another (i.e. dz=2 mm, numbers in millimeters referring to the actual size of the internal organ) and may comprise pixels of size 1 mm times 1 mm, i.e. dx=dy=1 mm. Then, each 3-dimensional image of the provided first 4-dimensional medical image may be converted into a voxel structure such that it consists of voxels with dx=dy=1 mm and dz=2 mm. Then, in step S200, each 3-dimensional medical image of the provided first 4-dimensional medical image may be re-scaled such that it consists, after re-scaling, of voxels with dx=dy=dz=dk, wherein dk may e.g. be set to 4 mm according to one of the options described above. Accordingly, the total number of voxels decreases by a factor of 32, the resolution in both x-direction and y-direction by a factor of 4 each, and the resolution in z-direction by a factor of 2.

The steps of generating a voxel structure from a multi-slice structure of two-dimensional slices with pixels and the step of re-scaling the generated voxels may be integrated, i.e. voxels of the desired dimensions may be directly generated from the multi-slice structure using known interpolation techniques. In the above example, the voxels may be directly generated with a dimension of dx=dy=dz=dk=4 mm.

Re-scaling the 4-dimensional medical image may also comprise automatically determining a size of the 4-dimensional medical image in at least one spatial dimension and automatically determining a scaling factor for the at least one spatial dimension based on the determined size such that the re-scaled 4-dimensional medical image has a size in the at least one spatial dimension equal to a predefined size for the at least one spatial dimension. This corresponds to a normalizing of heart sizes.

Re-scaling has the advantage that the provided first 4-dimensional medical image may be adapted to an expected, or ideal, resolution for the first 4-dimensional medical image in each spatial dimension, in particular to a resolution with and/or for which any or all of the artificial neural networks described in the following have been trained.

Preferably, the step S200 comprises a down-scaling of the provided first 4-dimensional medical image 20 in at least one spatial dimension (x, y and/or z) in order to reduce the resolution of the provided first 4-dimensional medical image in said at least one spatial dimension and/or to make this resolution the same as the resolution used by an artificial neural network during training. Any known down-scaling technique may be applied (nearest-neighbour interpolation, trilinear interpolation and/or the like). Down-scaling also reduces computational complexity and therefore decreases the requirements regarding computational power.

As illustrated in FIG. 2, in the system 1000 step a first re-scaling module 200 may be implemented by the computing device 1100. The first re-scaling module 200 is configured to spatially re-scale, in particular spatially up-scale and/or down-scale the first 4-dimensional medical image 20 as provided by the first input module 100. For this task, the first re-scaling module 200 may implement a re-scaling operation. The first 4-dimensional medical image is spatially re-scaled by re-scaling its 3-dimensional medical images at the different effective time points. The first re-scaling module 200 may up-scale the first 4-dimensional medical image 20 in one or two spatial dimensions and may down-scale the first 4-dimensional medical image 20 in one or two other spatial dimensions.

The first re-scaling module 200 is preferably configured to perform the step S200 in any of the variants described in the foregoing and vice versa. In particular, the first re-scaling module 200 may implement re-scaling by nearest-neighbour interpolation, trilinear interpolation and/or the like. In the case of a down-scaling, the first re-scaling module 200 may also be designated as a down-scaling module 200.

In a step S300, an at least partial segmentation of (or based on) the provided first 4-dimensional medical image 20 is generated, using at least one first trained artificial neural network 300 (in the presently described example a single first trained artificial neural network 300). If the optional step S200 has been performed, the segmentation may be generated based on the re-scaled (preferably down-scaled) version of the first 4-dimensional medical image 20 as illustrated in FIG. 2.

The trained artificial neural network 300 is preferably configured as a convolutional processing network with U-net architecture. The architecture is advantageously configured to process data in three spatial dimensions (x, y and z).

Each convolutional processing network comprises, apart from an input layer IN and an output layer OUT: a down-sampling path 310 comprising at least two processing convolutional blocks PB and at least two down-sampling blocks DS, and an up-sampling path 320 comprising at least two up-sampling blocks US and two processing convolutional blocks PB. The down-sampling path 310 generates an output 371 that may then be used directly as at least one (direct) input 373 for the up-sampling path 320. It will be described in the following that additional connections (or short-cuts) may exist between the down-sampling path 310 and the up-sampling path 320.

It is preferred that each up-sampling block US and each down-sampling block DS is followed, more preferably directly followed, by a processing convolutional block PB. It is also preferred that the trained artificial neural network 300 comprises the same number of up-sampling blocks US as of down-sampling blocks DS.

Down-sampling in at least one, or in all, of the down-sampling blocks DS is preferably done by 3-dimensional maxpooling, preferably with the same stride and the same kernel size for each of the three spatial dimensions. Also for this reason, it is beneficial to re-scale the provided first n-dimensional medical image such that the distances between the pixels (or voxels) are the same for all three spatial dimensions, dx=dy=dz=dk.

Optionally, at least one additional processing block 372 may be arranged between the output 371 of the down-sampling path 310 and the input 373 of the up-sampling path 320. In this way, the output 371 of the down-sampling path 310 may be used indirectly as input 373 for the up-sampling path 320. The additional processing block 372 may be designated as an "intermediate" processing block because of its position between the down-sampling block 310 and the up-sampling block 320.

Further details as well as variants and options for the trained artificial neural network 300 will be described in the following with respect to FIG. 3, FIG. 4 and/or FIG. 5. For example, the processing blocks may be so-called dense blocks, e.g. as described in Huang et al. Then, the convolutional processing network may also be designated as a convolutional dense network (or a "densely connected convolutional network" as in Huang et al.).

The output of the up-sampling path 320 enters the output layer OUT and is then output from the at least one first trained artificial neural network 300.

With respect to the system 1000, the computing device 1100 may be configured to implement the at least one first trained artificial neural network 300.

The at least one first trained artificial neural network 300 may provide one output value for each pixel (or voxel) of the 3-dimensional medical image input into the trained artificial neural network 300. That value preferably indicates a probability, for that pixel (or voxel) to belong to a specific structure or portion of the internal organ (i.e. to a specific label for that structure or portion) or to an optional "background" label. Accordingly, the output of the trained artificial neural network 300 may consist of a number, p, of probability masks 350-1, 350-2, . . . , 350-$p$ (hereafter sometimes referred to collectively as 350-$i$) indicating for all pixels (or voxels) a respective probability to belong to a specific structure of the internal organ or an optional "background" label.

The number p of different probability masks depends on how many structures are to be identified in the segmentation, either including or apart from an optional "background" label. Thus, the total number $N_{out}$ of output channels (or output nodes) may be equal to the number $N_v$ of voxels times (p or p+1) such that for each voxel a probability is output that it belongs to one of the p masks or to the background (+1).

Preferably, probability masks 350-$i$ for at least one, preferably multiple, more preferably for all of the following structure types of the heart are generated as part of generating the segmentation:

at least one blood cavity (i.e. blood-carrying structures);
at least one muscle tissue;
at least one valve structure;
at least one implant;
at least one anomaly;
at least one non-visible structure.

At least one blood cavity for which probability masks 350-$i$ are generated may in particular comprise, or consist of, any, or any combination, of the following:

at least one heart chamber (Right Atrium, Right Ventricle, Left Atrium, Left Ventricle), preferably all heart chambers;
the Coronary Sinus
at least one coronary artery (Right Coronary Artery, Left Coronary Artery), preferably both coronary arteries, optionally each with following branches;
inferior and/or superior Vena Cava;
pulmonary veins and respective orifices into the Left Atrium;
the Aorta;
the Aortic Root (i.e. valvular leaflets);
the Pulmonary Artery, optionally with its branches;
the Left Atrial Appendage;
the Left Ventricular Outflow Tract.

At least one muscle tissue for which probability masks 350-$i$ are generated may in particular comprise, or consist of, any, or any combination, of the following:

the myocardium of the Left Ventricle;
the myocardium of the Right Ventricle;
the myocardium of the Left Atrium;
the myocardium of the Right Atrium;
the atrial septum;
the papillary muscles (or a specific papillary muscle connected to a specific leaflet or specific region of a leaflet of an atrioventricular valve);

the Apex of the Left Ventricle and/or the Apex of the Right Ventricle.

At least one valve structure for which probability masks 350-$i$ are generated may in particular comprise, or consist of, any, or any combination, of the following:
- at least one leaflet of at least one atrioventricular valve (mitral valve, tricuspid valve);
- at least one annulus structure of at least one valve, especially of an atrioventricular valve;
- the aortic valve (orifice of the Right Coronary Artery and the Left Coronary Artery);
- a leaflet (cusp of the Aortic Valve and/or a leaflet (cusp) of the Pulmonic Valve;
- at least one trigone of an atrioventricular valve, in particular the mitral left and/or mitral right trigone;
- at least one commissure of at least one heart valve.

The leaflets or cusps may in the present method then be segmented directly (i.e. be provided with their own labels). The annulus structure and/or the leaflets or cusps may then be used to approximate commissures of the at least one heart valve which may be useful for implant planning, e.g. in Transcatheter heart valve interventions.

At least one implant for which probability masks 350-$i$ are generated may in particular comprise, or consist of, any, or any combination, of the following:
- an artificial pacemaker;
- a valve implant, preferably including a classification of the valve implant.

At least one anomaly for which probability masks 350-$i$ are generated may in particular comprise, or consist of, any, or any combination, of the following:
- a calcification, preferably in a region of a valve;
- a defect or morphologic abnormality of a heart valve, preferably including a classification of the defect or abnormality (e.g. valve prolapse, ruptured chordae, valve stenosis, incomplete coaptation and/or a leakage between closed leaflets);
- a thrombus, in particular a clot at a heart valve, the Left Atrial Appendage or the atrial septum;
- an aneurysm;
- a tumor;
- an infarct and/or stenosis of Coronary Arteries.

At least one non-visible structure for which probability masks 350-$i$ are generated may in particular comprise, or consist of, the AV node (Triangle of Koch). Such non-visible structure may e.g. be segmented due to surrounding 3D information and/or anatomical markers which will be taken into account and/or learned by the at least one first trained artificial neural network.

A background may also be provided with a probability mask 350-$i$ to be generated.

In some variants, in a step S400, automatically each pixel (or voxel) is assigned to a specific label to which the pixel (or voxel) belongs with the highest probability. In the system 1000, this may be implemented by a classifying module 400 run by the computing device 1100.

In an optional step S500 which is performed only in variants in which also step S200 has been performed, the output of step S400 or the classifying module 400, respectively, is then re-scaled, preferably such as to exactly compensate the effects of the re-scaling in the optional step S200. Since in step S200 preferably a down-scaling is performed, correspondingly in step S500 preferably an up-scaling is performed. In the system 1000, step S500 may be implemented by a second re-scaling module 500. In the case of an up-scaling, the second re-scaling module 500 may also be designated as an up-scaling module 500.

Up-scaling by the second re-scaling module 500 may in particular be realized by interpolation of new pixel (or voxel) probability values between the pixels (or voxels) of the probability masks 350-$i$ output by the trained artificial neural network 300. In some variants, nearest-neighbour-interpolation or trilinear interpolation may be used.

The result of step S500 after step S400 has been previously performed, will be a number, p, of labels 550-1, 550-2, . . . , 550-$p$ (hereafter also sometimes collectively referred to as 550-$i$) provided sized such as to exactly fit to the provided first 4-dimensional medical image 20 and/or at least one of the 3-dimensional medical images of the 4-dimensional medical image, preferably before the application of step S200.

In some variants, step S400 may be performed after step S500. In other words, the re-scaling in step S500 may be performed not on the labels 550-$i$ but on the probability masks 350-$i$, and step S400 is then performed not on the original probability masks 350-$i$, but on probability masks 350-$i$ re-scaled (preferably: up-scaled) by step S500.

Referring back to FIG. 1, in a step S600, a 4-dimensional medical image segmentation 60 is generated based at least on the segmentation generated by the at least one first trained artificial neural network 300 in step S300. In some variants, the same steps as described in the foregoing may be applied to the 3-dimensional medical images for each effective time point of the provided first 4-dimensional medical image. The segmentations generated for the 3-dimensional medical images may then be associated with their respective effective time points and the result may be provided as the 4-dimensional medical image segmentation 60.

The provided 4-dimensional medical image segmentation 60 may be provided to a display device and be used thereby e.g. as an overlay over real-time-acquired medical image data (e.g. two-dimensional fluoroscopy data). For example, in a real-time view of a human heart, a current cardiac cycle of that heart may be automatically detected, and the generated 4-dimensional medical image segmentation 60 of that same heart (from medical image data previously taken from the patient) may be adjusted by, among other operations such as re-positioning and re-orienting, re-scaling:
a) the effective time dimension to fit the current cardiac cycle (in particular in combination with a re-positioning, or shifting, of the generated 4-dimensional medical image segmentation 60 to fit the current cardiac cycle of the heart stage by stage) and
b) the size of the generated 4-dimensional medical image segmentation 60 (in particular, of the labels or masks) to the size of the human heart as it is displayed by the display device.

The provided 4-dimensional medical image segmentation 60 which will in various embodiments comprise a discrete number of 3-dimensional medical image segmentations for different effective time points may be adjusted to fit as accurately as possible the—usually continuously acquired and displayed—current cardiac cycle of the heart.

The generated 4-dimensional medical image segmentation 60 re-scaled, re-oriented and/or re-positioned in that way may then be displayed by the display device as an overlay over the real-time view of the human heart and/or over CT or MR image data. It should be understood that the same steps may be performed for other internal organs than the human heart, in particular for internal organs that exhibit cyclic movements or behavior such as e.g. the lungs.

Accordingly, the system 1000 may comprise a display device 1200 operatively connected to the computing device 1100 and configured to display both a real-time view of a human organ (e.g. a human heart) and the 4-dimensional medical image segmentation 60 re-scaled, re-oriented and/or re-positioned to fit that real-time view in spatial and temporal dimensions. The display device 1200 comprises an interface for receiving the real-time-view of the human organ (e.g. human heart) from a medical imaging device 1300 which may also be part of the system 1000 but which may also be external to the system 1000. Data received from the medical imaging device 1300 may be used by the computing device 1100 to re-scale, re-orient and/or re-position the generated 4-dimensional medical image segmentation 60 to fit the real-time view provided by the medical imaging device 1300. A data connection between the medical imaging device 1300 and the computing device 1100 may be realized directly, or via the display device 1200 and/or via a wireless and/or Internet connection.

At least one predetermined structure, for example an annulus structure, may be segmented volumetrically, i.e. as a tubular structure.

In the system 1000, generating the 4-dimensional medical image segmentation 60 may be performed by an output module 600 of the system 1000 which may perform step S600 as described above or according to any of the options and variants further described herein. In FIG. 2, the arrow entering the output module 600 from the left indicates optional further labels 550-$i$ being provided to the output module 600 based on a 3-dimensional medical image for each of at least one other effective time points.

The generated 4-dimensional medical image segmentation 60 may also be adapted (in particular, re-sized and/or positioned) to fit the at least one original medical image 10. Accordingly, a further 4-dimensional medical image segmentation may be generated which comprises the labels, as generated using the first trained artificial neural network 300 based on the first provided medical image 20 and the at least one original medical image 10, wherein either or both are adapted (re-sealed, re-positioned and/or the like) to fit the respective other.

In the following other variants and methods for generating the 4-dimensional medical image segmentation 60 will be explained in detail.

Figure 3:
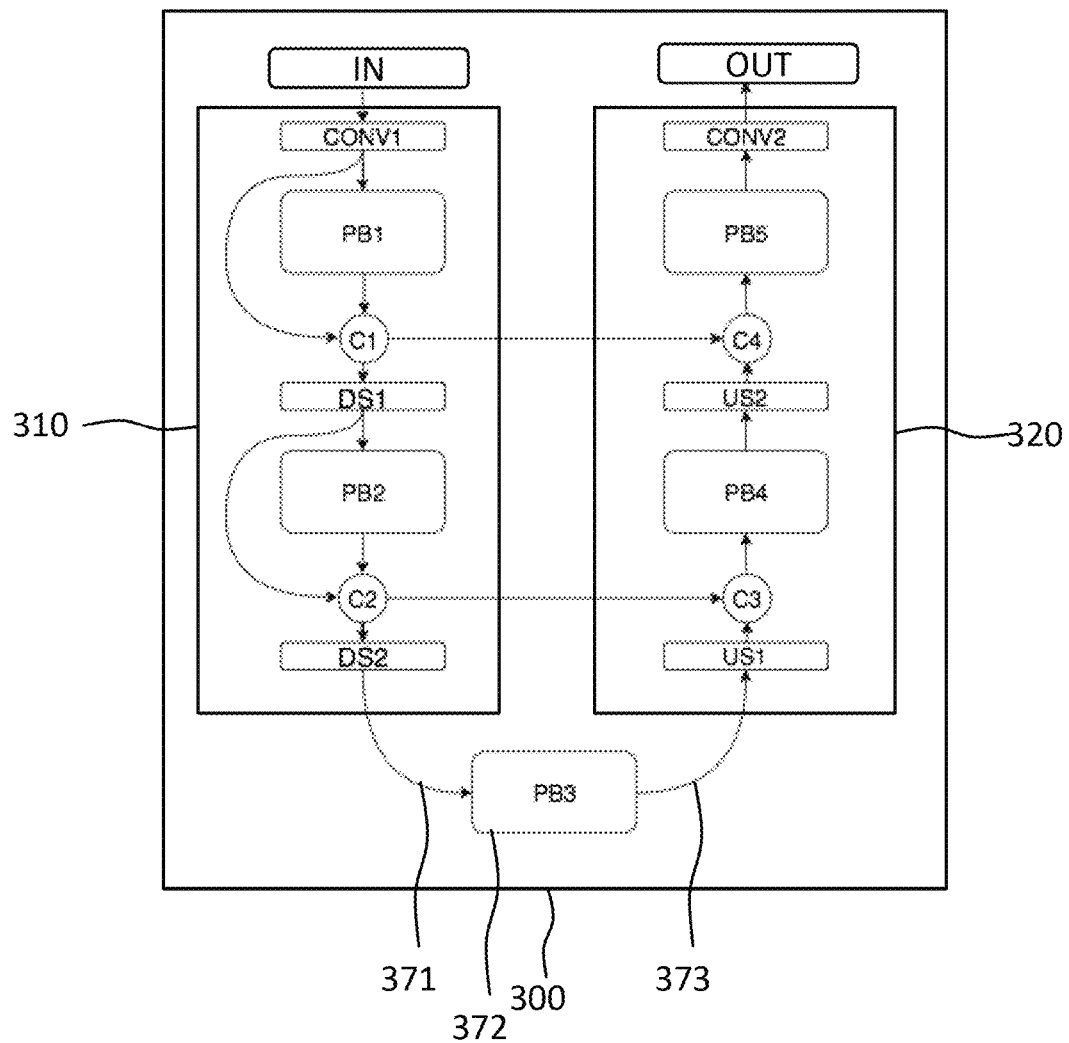
FIG. 3 illustrates an advantageous optional internal structure of a trained artificial neural network.

First, however, possible details of the first trained artificial neural network 300 of the method according to FIG. 1 and/or of the system 1000 of FIG. 2 are explained with respect to FIG. 3.

FIG. 3 illustrates optional details of the first trained artificial neural network 300 with the down-sampling path 310 and the up-sampling path 320 as already shown in FIG. 2.

In some variants, as shown in FIG. 3, the down-sampling path 310 is realized in as a feed-forward path with at least one first convolutional layer CONV1 following after the input layer IN. The output of the at least one first convolutional layer CONV1 is fed forward to the first processing block PB1 but is also concatenated with the output of the first processing block PB1 in a first concatenation block C1.

Continuing within the down-sampling path 310, the output of the first concatenation block C1 is fed into a first down-sampling block DS1 of the down-sampling path 310. The output of the first down-sampling block DS1 is fed forward into a second processing block PB2, but is also concatenated, in a second concatenation block C2, with the output of the second processing block PB2. Then, the output of the second concatenation block C2 is fed forward into a second down-sampling block DS2 of the down-sampling path 310.

The output 371 of the down-sampling path 310 is first processed by a third processing block PB3 before being fed into the up-sampling path 320. Alternatively, the third processing block PB3 may be associated either with the down-sampling path 310 or with the up-sampling path 320.

The output of the third processing block PB3 is fed forward into a first up-sampling block US1 of the up-sampling path 320. The output of the first up-sampling block US1 is concatenated, in a third concatenation block C3, with the output of the second concatenation block C2, and the output of the third concatenation block C3 is then fed forward to a fourth processing block PB4.

The output of the fourth processing block PB4 is fed forward into a second up-sampling block US2. The output of the second up-sampling block US2 is concatenated, in a fourth concatenation block C4, with the output of the first concatenation block C1. The output of the fourth concatenation block C4 is then fed forward into a fifth processing block PB5, the output of which is then fed forward into a second convolutional layer CONV2, the output of which is then fed forward to the output layer OUT.

Each up-sampling block US2 may be realized as applying a 3D-spline interpolation method, e.g. of order 0 (i.e. nearest-neighbour), of order 1 (trilinear interpolation) and/or the like.

The sequence of first a down-sampling path 310 and then an up-sampling path 320 is referred to as a U-net architecture.

Each processing block may in particular be realized according to one of the following options:

According to a first option, a processing block PBi may be realized as dense block (see e.g. Huang et al.), but realized with 3-dimensional convolutional filters instead of 2-dimensional convolutional filters, in particular as a dense block of composite layers with a bottleneck structure with 3-dimensional convolutional filters.

Figure 4:
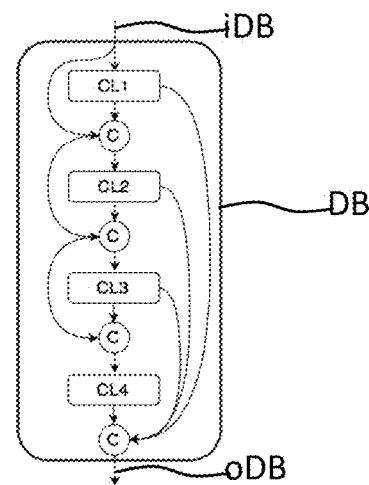
FIG. 4 illustrates an advantageous optional internal structure of a processing block realized as a dense block.

FIG. 4 illustrates a possible advantageous internal structure of a processing block PBi realized as a dense block DB.

Each dense block DB may comprise a plurality of composite layers CLi connected in a feed-forward structure. An input iDB to a dense block DB may be first fed into a first composite layer CL1, and may also be concatenated with the output of the first composite layer CL1. The result of the concatenation is then fed into a second composite layer CL2. The output of the second composite layer CL2 is concatenated with the input of the second composite layer CL2, and the result of the concatenation is used as input of a third composite layer CL3. The output of the third composite layer CL3 is concatenated with the input of the third composite layer CL3 and fed into a fourth and (in this example) last composite layer CL4.

The output of the last composite layer CL4 is concatenated with the outputs of all of the previous composite layers CL1, CL2, CL3, and the output of said concatenation is then provided as an output oDB of the dense block DB. It shall be understood that any other number of composite layers CLi other than four may also be used and that four has been used as one preferred option that does not exclude other numbers of composite layer CLi being provided, e.g. three composite layer CLi or five or more composite layer CLi.

The above described procedure may be generalized as follows: the first composite layer CL1 receives the input iDB of the dense block DB as input. The output of the first composite layer CL1 is concatenated with the input iDB of the dense block DB and the result of the concatenation is provided as input to the second composite layer CL2. For the second and each following composite layer CL2 except the last one, always the output of a composite layer CLi is concatenated with its input, and the result of the concatenation is provided to the next composite layer CL(i+1). The output of the last composite layer CL4, finally, is only concatenated with the outputs of all the previous composite layer CLi, and the result of that concatenation is provided as output oDB of the dense block DB.

In all of this it should be understood that each block or composite layer in general will still process 3-dimensional data even if the number of channels for a specific composite layer may be much larger than the total number of pixels or voxels in the 3-dimensional medical image. The number of input channels of each composite layer CLi will in general be different, whereas the number of output channels of each composite layer CLi is preferably the same.

Figure 5:
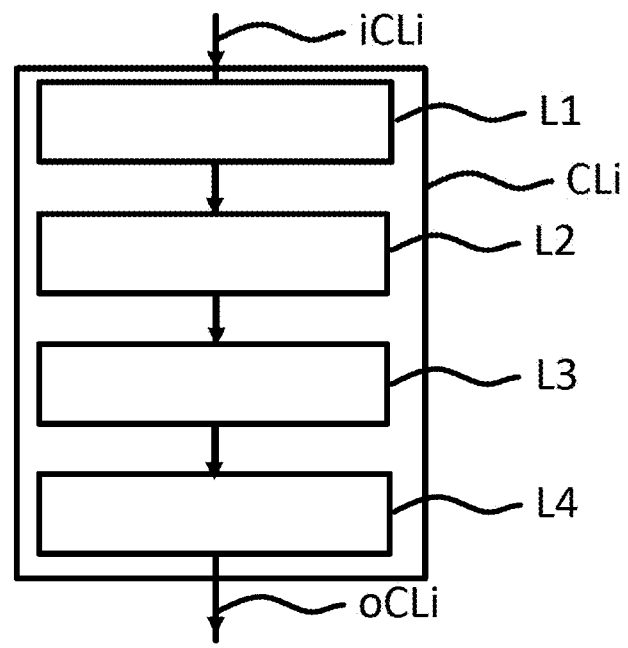
FIG. 5 illustrates an advantageous optional internal structure of a composite layer of a dense block.

FIG. 5 illustrates a possible advantageous internal structure of a composite layer CLi of a dense block DB.

The composite layers CLi may preferably comprise layers (or sets of layers) L1, L2, L3 and L4, wherein L1 receives the input iCLi of the composite layer CLi and feeds its own output forward into L2 which feeds its own output forward into L3 which feeds its own output forward into L4 which provides its own output as an output oCLi of the composite layer CLi.

The first layer L1 comprises, or consists of, a q×q×q ("q times q times q") convolutional layer, q being an integer, preferably 1. The q×q×q convolutional layer in general has m input channels and k output channels, wherein m is different for each composite layer CLi in a dense block DB and k is a constant for each dense block DB, k<m.

The second layer L2 is a non-linearity layer comprising a non-linear function (such as a rectified linear unit, ReLU, or, preferably, an exponential linear unit, ELU), optionally in combination with a batch norm.

The third layer L3 comprises, or consists of, a 3-dimensional r×r×r ("r times r times r") convolutional layer, r being an integer larger than q (r>q), for example, q=3 or q=5. Preferably, the third layer L3 has k input channels and k output channels. The third layer L3 may also be replaced by an atrous spatial pyramid pooling block, ASPP, e.g. as described (for 2-dimensional convolutional layers) in the scientific publication by Chen et al.: "DeepLab: Semantic Image Segmentation with Deep Convolutional Nets, Atrous Convolution, and Fully Connected CRFs", arXiv: 1606.00915v2 of 12 May 2017, hereafter cited as "Chen et al.".

The fourth layer L4 is a second non-linearity layer comprising a non-linear function (such as a rectified linear unit, ReLU, or, preferably, an exponential linear unit, ELU), optionally in combination with a batch norm.

According to a second option, a processing block PBi may be realized as a set of parallel 3-dimensional convolutional layers with different dilation rates (or: different strides). The output of the parallel convolutional layers may be concatenated to form the output of the processing block PBi, or so-called pyramid pooling (see Chen et al.) may be applied. In particular the processing block PB may be realized as an atrous spatial pyramid pooling block, ASPP.

For example, a processing block PBi may comprise a first convolutional layer with a 3×3×3 ("3 times 3 times 3") convolutional kernel which evaluates not a pixel and its 26 next neighbours (i.e. uses a stride of 1 in each of the three spatial dimensions) but uses a stride of 2 in each of the three spatial dimensions. The processing block PBi may also comprise a second convolutional layer with a 3×3×3 convolutional kernel with a stride of 3, a third convolutional layer with a 3×3×3 convolutional kernel with a stride of 4 and so on, for a given maximum number of strides.

According to a third option, a processing block PBi may be realized as a single 3-dimensional convolutional layer or as a series of feed-forward 3-dimensional convolutional layers. This third option is advantageous for use in a second trained artificial neural network (e.g. as described in further detail in the following) which can be less complex in order to save computational resources.

As has been described in the foregoing, all of the processing block PBi of the trained artificial neural network 300 may be realized in the same way (e.g. according to one of the discussed first, second or third option), or one or more of the processing blocks PBi of the trained artificial neural network 300 may be realized differently than one or more others of the processing blocks PBi.

In the foregoing, it has been described how in step S600, the results (labels) of performing steps S100 through S500 for each effective time point (e.g. percentage of the cardiac cycle) for which 3-dimensional medical image data are provided (or: comprised) by the provided first 4-dimensional medical image 20 are gathered and put together to generate a 4-dimensional medical image segmentation. This approach has the advantage that only one artificial neural network 300 has to be trained so that all available training data for all effective time points can be used for training the artificial neural network 300. This is a considerable advantage since well-labelled training data of internal organs are difficult to produce in sufficient quantity.

In some advantageous variants, the step S100 of providing the first 4-dimensional medical image may comprise using a second trained artificial neural network, in particular to determine a region of interest in a provided second 4-dimensional medical image, the region of interest then being used as the provided first 4-dimensional medical image 20.

One advantage provided by this variant is that the medical image provided to the first trained artificial neural network 300 do not have to be selected and cropped manually but that the selection of a region of interest and of cropping the medical image down to that region of interest is performed automatically. In some advantageous embodiments, the second trained artificial neural network may generate a plurality of regions and a specific region of the generated plurality of regions may be selected as the region of interest.

Figure 6:
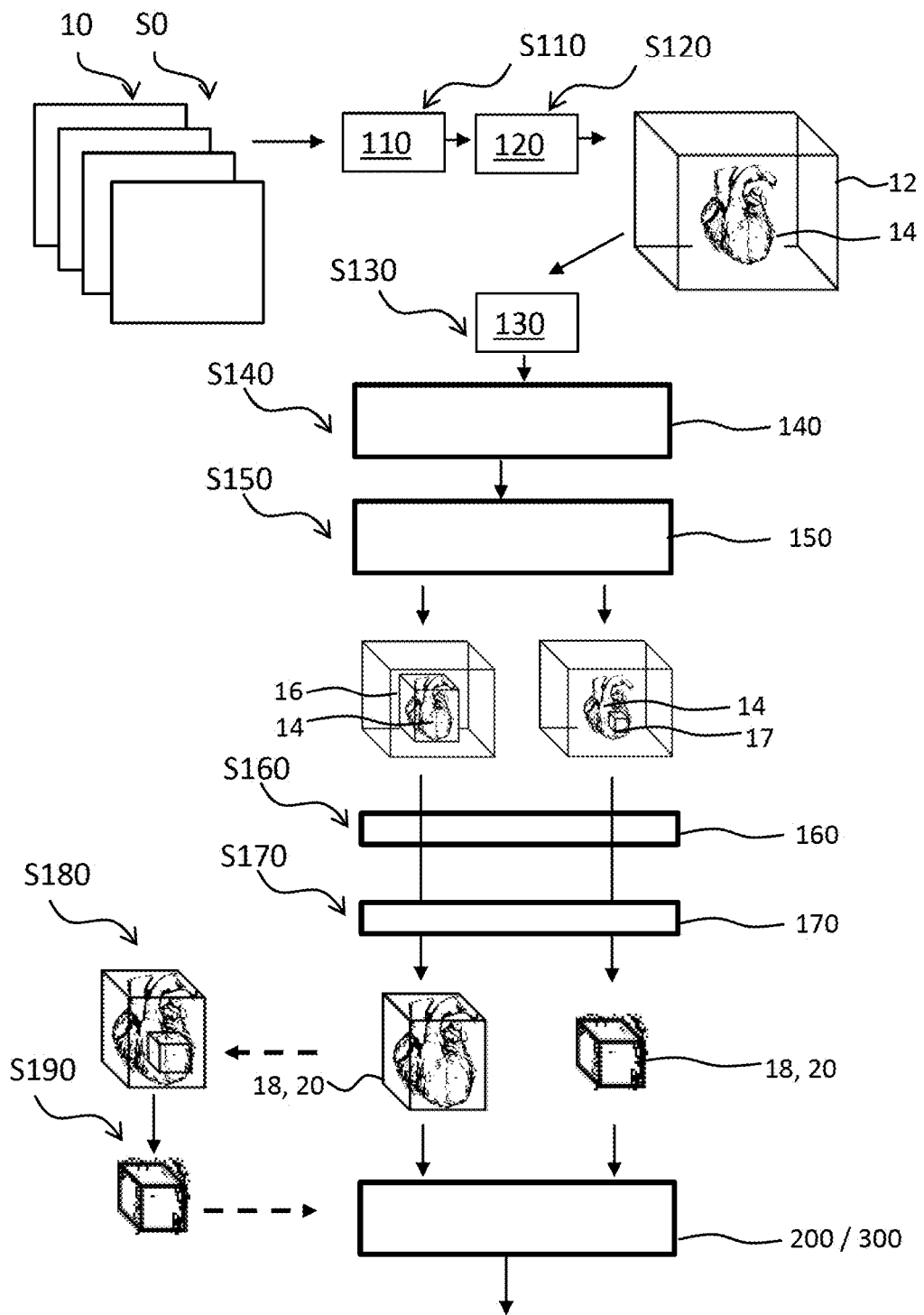
FIG. 6 illustrates advantageous optional details of one of the steps of the method of FIG. 1.
Figure 7:
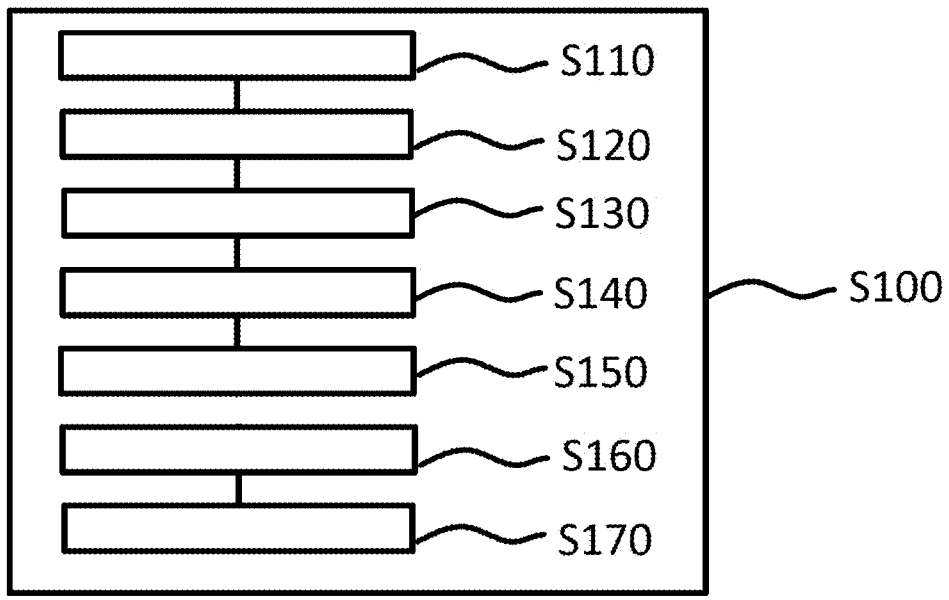
FIG. 7 illustrates a schematic flow diagram of a method according to the optional details of FIG. 6.

FIG. 6 illustrates advantageous optional details of step S100 of the method of FIG. 1 in addition to the sub-steps already described for step S100 in the foregoing. FIG. 7 shows a schematic flow diagram illustrating step S100 according to said advantageous optional details in more detail.

In an optional sub-step S110 of step S100, data normalization is performed, e.g. as has been described in the foregoing with respect to FIG. 2, on the at least one original medical image 10. The sub-step S110 may be performed by a data normalization sub-module 110 of the input module 100 implemented by the computing device 1100. In a sub-step S120 of step S100, at least one voxel structure may be generated from the at least one original medical image 10 in order to provide (or: generate) a second 4-dimensional medical image 12. Preferably, one voxel structure per effective time point comprised (or described) in the at least one medical image 10 is generated. The sub-step S120 may be performed by a voxel-generating sub-module 120 of the input module 100, as has been described with respect to step S100 and FIG. 2 in the foregoing.

In an optional sub-step S130 of step S100, the voxel structure of the second 4-dimensional medical image 12 may also be re-scaled into a re-scaled 4-dimensional voxel structure, or, in other words, into a re-scaled version of the second 4-dimensional medical image 12. Re-scaling a 4-dimensional voxel structure in particular means a spatial re-scaling of each 3-dimensional voxel structure for each effective time point.

The re-scaling may be performed in particular in the same way as has been described with respect to step S200 and the provided first 4-dimensional medical image 20, i.e. the resolution of each of the 3-dimensional medical images of the second 4-dimensional medical image 12 may be re-scaled in any or all spatial dimensions in order to reach a predetermined resolution for each spatial dimension, preferably the same predetermined resolution (voxel/dk) for all three spatial dimensions.

The re-scaling (preferably down-scaling) in the optional sub-step S130 may be performed by a re-scaling sub-module 130 (in particular: a down-scaling module) of the input module 100. By the sub-steps S110, S120 (and optionally step S130), thus the second 4-dimensional medical image 12 is provided. If step S130 is performed, the second 4-dimensional medical image before its re-scaling in step S130 may be designated as "intermediate 4-dimensional medical image" or as the not-re-scaled version of the provided second 4-dimensional medical image 12. As has been described also with respect to the first n-dimensional medical image 20, the second 4-dimensional medical image 12 may alternatively be simply read out from an archiving system or downloaded from a cloud storage or the like.

In FIG. 6, the second 4-dimensional medical image 12 is illustrated as a sketch of a human heart 14 within a larger box which symbolizes the entirety of the second 4-dimensional medical image 12. For example, the 4-dimensional medical image 12 may comprise image data not only about the human heart 14 but also of surrounding tissue, internal organs, bones and so on.

In a sub-step S140 of step S100, a segmentation of at least part of the second 4-dimensional medical image 12 is generated using at least one second trained artificial neural network 140 configured as a convolutional processing network with U-net architecture. "At least part" here in particular means that, in case the second n-dimensional medical image 12 is a 4-dimensional medical image 12, each 3-dimensional medical image (one for each effective time point) may be processed separately by a separate instance of the second trained artificial neural network 140 or only the 3-dimensional medical image for one effective time point may be processed. When the second n-dimensional medical image 12 is a 3-dimensional medical image, then preferably the complete second medical image 12 is processed by the second trained artificial neural network 140.

The second trained artificial neural network 140 may be configured with the same types of blocks as the first artificial neural network 300, e.g. with the same structure as described with respect to FIG. 3 and/or any or all options and variants described with respect to thereto, in particular with respect to FIG. 4 and FIG. 5.

However, since the purpose of the second trained artificial neural network 140 is to pre-select regions of interest within the provided second n-dimensional medical image 12, it may be designed with less complexity than the first trained artificial neural network 300.

For example, the second trained artificial neural network 140 may be provided with less processing blocks PBi than the first trained artificial neural network 300 and/or its processing blocks PBi may be provided with less layers. For example, if any dense blocks DB according to the first option described for the processing blocks PBi in the foregoing are used, they may be provided with less composite layers CLi.

Additionally or alternatively, if any processing blocks PBi according to the second option described for the processing blocks PBi in the foregoing are used, those processing blocks PBi may be provided with less convolutional filters than their counterparts at the same position in the first trained artificial neural network 300.

Based on the segmentation generated by the second trained artificial neural network 140, in a sub-step S150 of step S100 a portion 16 of the segmentation for the second n-dimensional medical image 12 is determined which comprises the structure of the internal organ, in the present example the human heart 14.

As is illustrated in FIG. 6, more than one portion 16, 17 may be determined in step S150, i.e. at least one portion 16, 17 may be determined in step S150. Some of the determined portions 16, 17 may overlap each other, some may be completely overlapped by at least one other determined portion 16, and/or the like.

For example, one determined portion 16 may correspond to the entire human heart, and another determined portion 17 may correspond to a region of particular interest such as a region around a heart valve (optionally including coronary arteries). In another example, a first determined portion may correspond to a region around the tricuspid valve of the human heart, and a second determined portion may correspond to a region around the mitral valve of the human heart, wherein the two determined portions may overlap or may be separate.

In this example where the internal organ of interest is a human heart 14, the determined portion 16, 17 may comprise the human heart, and optionally at least one blood vessel connected to it.

The determining in sub-step S150 may be performed automatically, e.g. based on a predefined criterion set for the method, for example by a determining sub-module 150 of the input module 100. For example, a user may, in a GUI operatively connected to the determining module 150, select that the user is interested in a particular internal organ (e.g. the human heart 14) and/or a particular intervention (e.g. a transcatheter heart valve intervention). In a database (e.g. a computer memory of the system 1000), said choice of the user may be associated with a list of structures or region of interests that are defined to belong to the selected particular organ and/or particular intervention. In the case of the human heart 14, the list may comprise the heart chambers, their surrounding muscle tissue, and so on.

Additionally or alternatively, the user may be presented, by the GUI, with a choice to select any structures that are of interest to the user. For example, the user may be presented with a list of all structures that have been labelled by the second trained artificial neural network 140 and/or, when the user has selected a particular organ of interest, with a suggestion of which structures are associated with the selected particular organ (e.g. human heart 14).

The user may be presented, by the GUI, with a view of 3-dimensional graphical representations of the selected structures (e.g. the human heart 14) according to the segmentation and with a box-shaped three-dimensional frame cropped to the minimum size necessary to include all of the selected structures, i.e. the complete portion 16 of the segmentation determined in step S150 as illustrated in FIG. 6. The user can then make an informed decision about whether or not any additional structures should be included in the selection or excluded from the selection. In some embodiments, the view may be a real-time view.

In a sub-step S170 of step S100, at least one portion 18 of the provided second n-dimensional medical image 12 (in its version before the optional re-scaling in step S130) corresponding to the determined portion 16 of the segmentation for the second n-dimensional medical image 12 is extracted, for example by an extracting sub-module 170 of the input module 100. Said extracted portion 18 preferably comprises, or consists of, a 3-dimensional portion out of each 3-dimensional medical image of the provided second n-dimensional medical image 12 (i.e. for each effective time point), each 3-dimensional portion having a necessary position, orientation and minimum size such as to encompass the complete portion 18 corresponding to the determined portion 16, 17 of the segmentation determined in step S140.

Extracting the at least one portion 18 in sub-step S170 may optionally be preceded, when the second n-dimensional medical image 12 has been re-scaled in the optional sub-step S130 before being input into the second trained artificial neural network 140, by re-scaling the determined portion 16, 17 of the segmentation for the second n-dimensional medical image 12 to compensate any changes in any resolution made in sub-step S130 to the second n-dimensional medical image 12 before the segmentation. Extracting S170 the portion 18 may also comprise shifting the determined portion 16 of the segmentation in order to fit the second n-dimensional medical image 12.

The re-scaling in the optional sub-step S160 may be provided by an optional re-scaling module 160, in particular an up-scaling module. In particular, when in sub-step S130 the second n-dimensional medical image 12 has been down-scaled (as is preferred), then sub-step S160 may be applied to perform a compensating up-scaling such that the determined portion 16, 17 fits the corresponding portion to be extracted from the provided second n-dimensional medical image 12 (in its version before the optional re-scaling in step S130).

Then, the at least one extracted portion 18 of the provided second n-dimensional medical image 12 is provided as the at least one first n-dimensional medical image 20, i.e. to the re-scaling module 200 as illustrated in FIG. 6 or directly to the first trained artificial neural network 300. In this way, it is ensured that the considerable computational resources needed for the at least one first trained artificial neural network 300 are used only on structures of interest and are not wasted on structures of an original medical image that are not relevant in the present context. Furthermore the down-scaling of the provided first n-dimensional medical image 20 can be done by a smaller factor or avoided, thus retaining a higher resolution and more details in the voxel data of the structures of interest, when using the voxel data as an input into the at least one first trained artificial neural network 300, which may be trained specifically on the structures of interest and a particular, higher resolution (smaller dk).

Optionally, as indicated by steps S180 and S190 in FIG. 6, the at least one extracted portion 18 of the provided second n-dimensional medical image 12 may again be used as an input (or, in other words, as a further second n-dimensional medical image 12), and the procedure as discussed with respect to FIG. 7 may be performed one or more additional times.

In this way, an ever more detailed and ever more accurately delimited portion of interest may be extracted from the originally provided second n-dimensional medical image 12 before the actual segmentation by the first trained artificial neural network 300 is performed. For example, from medical image data showing a human chest (as second n-dimensional medical image 12), a portion 18 indicating the human heart 14 could be extracted, and from that portion 18 (as another second n-dimensional medical image 12) a particular area of the human heart 14, e.g. a region around a heart valve, may be extracted as a further extracted portion 18 which is then provided, as the first n-dimensional medical image, to the input module 100.

However, a two-step approach wherein the extracted portion 18 is used as input for the first trained artificial neural network 300 (either with or without the re-scaling module 200 in between) is preferred. The inventors have found that this two-step approach allows maximum precision and accuracy without further similar steps being necessary.

If there is more than one extracted portion 18 (corresponding to more than one region of interest), the further steps of the method may be applied to the plurality of portions 18 consecutively or in parallel. For example, one first trained artificial neural network 300 trained for the region of interest represented by a first of the plurality of extracted portions 18 may be controlled to segment that first of the plurality of extracted portions 18, and, consecutively or in parallel, another first trained artificial neural network 300 trained for the region of interest represented by a second of the plurality of extracted portions 18 may be controlled to segment that first of the plurality of extracted portions 18, and so on for all other steps and/or modules. It is preferred that the first trained artificial neural networks 300 segment all of the plurality of extracted portions 18 in parallel; it is advantageous if the computing device implementing these first trained artificial neural networks 300 is a cloud computing device which offers a lot of parallel processing power.

It will be understood that the sub-steps S110-S170 may be implemented, in the system 1000, in the input module 100 in a straight-forward way using the same techniques as has been described with respect to the steps S100-S600. Similarly, a data normalization may be applied at any stage, for example to a generated voxel structure and/or to the extracted at least one portion 18.

In some embodiments, when the provided second medical image 12 is a 4-dimensional medical image with 3-dimensional images for each of multiple effective time points, steps S130-S160 may be performed only for one single effective time point (or for less effective time points than included in the provided second medical image 12). Then in S170 the corresponding portion 18 is extracted for each efficient time point of the provided second 4-dimensional medical image 12 (in its version before the optional re-scaling in step S130), based on the determined portion 16, 17 of the one single effective time point (or the less effective time points).

In the following, some advantageous variants will be described which make use of the fact that the 3-dimensional medical image data for different effective time point are similar to one another. In other words, the information that, for example, effective time point t2 is between effective time point t1 and effective time point t3 may be used to label the 3-dimensional medical image at effective time point t2 more accurately after the 3-dimensional medical image segmentations and/or latent representations and/or hidden states for the effective time point t1 and for the effective time point t3 are known. Similarly, the generated 3-dimensional medical image segmentation for the effective time point t1 and/or the effective time point t3 may be repeated or amended based on the 3-dimensional image segmentation and/or latent representations and/or hidden states for the effective time point t2.

One advantageous option is to include a recurrent layer in the first trained artificial neural network 300 and to allow at least one latent representation (or hidden state) of a first instance of the first trained artificial neural network 300 processing a 3-dimensional medical image for a first effective time point to be used as input for that recurrent layer in a second instance of the first trained artificial neural network 300 processing a 3-dimensional medical image for at least one second (or preferably all other) effective time points. The recurrent layer may be realized e.g. as a long-short-term-memory layer (LSTM layer).

These advantageous options, as well as any other options described herein in the foregoing and/or in the following should be understood to be equally applicably to, or combinable with, any of the second trained artificial neural networks 140 described.

For example, the recurrent layer may be arranged, in the architecture of the trained artificial neural network 300 of FIG. 3, between the third processing block PB3 and the up-sampling path 320, i.e. such that it received an output of the third processing block PB3 as input and feeds its own output as input to the up-sampling path 320. The connection between a first instance of the first trained artificial neural network 300 processing 3-dimensional medical image for a first effective time point and a second instance of the first trained artificial neural network 300 processing 3-dimensional medical image for a second effective time point may be realized by providing the output of the third processing block PB3 of the first instance as input to the recurrent layer of the second instance.

In some advantageous variants, the output of the third processing block PB3 of each instance of the first trained artificial neural network 300 is used as input for the recurrent layer of each instance of the first trained artificial neural network 300 processing a 3-dimensional medical image at a later effective time point, optionally only up to a predefined number of effective time point steps.

In other words, e.g. when the provided first 4-dimensional medical image 20 comprises 3-dimensional medical images for each of ten effective time points, namely for 0%, 10%, . . . 90% of the cardiac cycle, then the following structure may be set up in a method or in the system 1000:

A first instance of the first trained artificial neural network 300 may be set to process the 3-dimensional medical image for (or: at) a first effective time point (t1=0%), a second instance may be set to process the 3-dimensional medical image for a second effective time point (t2=10%) and so on up to a tenth instance set up to process the 3-dimensional medical image for a tenth effective time point (t10=90%).

Then, the output of the third processing block PB3 of the first instance will be provided to the recurrent layer of each of the second through tenth instance; the output of the third processing block PB3 of the second instance will be provided to the recurrent layer of each of the third through tenth instance, and so on.

Optionally, the number of effective time points to which latent representations (e.g. the output of the third processing block PB3) may be transmitted may be limited, e.g. the first instance providing the output of its third processing block PB3 only to the second and third instance (e.g. up to two effective time point steps), the second instance only to the third and fourth instance, and so on. The maximum number of effective time point steps is a hyper parameter.

Since the last effective time point of a cycle (e.g. cardiac cycle) may be seen as being followed by the first effective time point of the cycle, the feeding of outputs of e.g. the third processing block PB3 to instances of the first trained artificial neural network for "later" effective time points may be continued over the "last" effective time point (e.g. t10=90%) by treating the last effective time point as being followed by the first effective time point (e.g. t1=0%), and by running instances for at least some of the effective time point more than once. For example, in case of the maximum number of effective time point steps being set to 2, the output of the third processing block PB3 of the ninth instance will be provided as input to the recurrent layer of the tenth instance as well as to the recurrent layer of the first instance which will then be run a second time, and so on, for a predetermined number of runs of each instance. Alternatively, the feeding of outputs of instances of the first trained artificial neural network to other instances of the first trained artificial neural network may be performed in opposite direction, e.g. backwards from 90% to 0% of the cardiac cycle.

It will be understood that the results of running each instance more than once, each time receiving richer and richer information from the other instances, will continuously improve the segmentation at the cost of increased need for computational resources and time.

Additionally or alternatively, the output of the third processing block PB3 of each instance of the first trained artificial neural network is used as input for the recurrent layer of each instance of the first trained artificial neural network processing a 3-dimensional medical image at an earlier effective time point, optionally again up to a predefined number of effective time point steps.

The two variants may also be combined such that each instance is run once starting consecutively with the instance processing the earliest effective time point, each instance feeding its output of its third processing block PB3 to instances processing later effective time points, that then each instance is run once starting consecutively with the instance processing the latest effective time point, each instance feeding its output of its third processing block PB3 to instances processing earlier effective time points.

It should be understood that although mention has been made of the third processing block PB3, in many variants and embodiments this third processing block PB3, being arranged between the down-sampling path 310 and the up-sampling path 320 will not actually be the third (in number) processing block along the U-net architecture, because the down-sampling path 310 may comprise more than two processing blocks PB. The term "third" processing block PB3 is used herein mostly as a designation and not necessarily as a counter (although in the embodiment of FIG. 3 the two uses of the term coincide).

Moreover, in some advantageous variants, the recurrent layer may be arranged at a different position of the U-net architecture of the first trained artificial neural network 300, for example, between the second convolutional layer CONV2 and the output layer OUT. The output of each instance used as input for that recurrent layer may then be provided by the second convolutional layer CONV2. All other options and variants may be provided as has been described in the foregoing with respect to the third processing block PB3.

In other words, in general at least one recurrent layer may be arranged within the U-net architecture of the first trained artificial neural network 300 and may be used to receive input from other instances processing different effective time points. Preferably, the inputs into each such recurrent layer are provided from a block immediately preceding the recurrent layer (in another instance).

For example: recurrent layers arranged after the third concatenation block C3 may receive as input the output of said third concatenation block C3 from other instances in one of the variants described in the foregoing (e.g. with respect to the maximum number of effective time point steps). Recurrent layers arranged after the fourth concatenation block C4 may receive as input the output of said fourth concatenation block C4 from other instances in one of the variants described in the foregoing (e.g. with respect to the maximum number of effective time point steps).

Recurrent layers may be arranged at several, or even all, of the described positions and used accordingly.

In some advantageous variants, a recurrent layer (e.g. an LSTM layer) may be arranged within, or before, the down-sampling path 310, and may be configured to receive a user input, or a signal based on a user input. For example, a user could be provided, by a GUI, with the opportunity to review a 3-dimensional medical image segmentation provided by one instance of the first trained artificial neural network 300, optionally starting with either the lowest or the highest available effective time point.

The user may then be given the choice to make adjustments to the 3-dimensional medical image segmentation, and a signal (in particular a signal representing a tensor such as a vector, a matrix, or a 3-dimensional array) based on the adjustments made by the user may then be input into the (or one of the) recurrent layer(s) of the instance for the next effective time point or as an additional (e.g. concatenated) input into the input layer for the next effective time point, and so on (going clock-wise, i.e. in the order of increasing effective time points or counter-clock-wise, i.e. in the order of decreasing effective time point).

Also in cases where no recurrent layer is present either before or within the down-sampling path 310, the user may then be given the choice to make adjustments to the 3-dimensional medical image segmentation 60, and a signal (in particular a signal representing a tensor such as a vector, a matrix, or a 3-dimensional array) based on the adjustments made by the user may then be input as an additional (e.g. concatenated) input into the input layer for the next effective time point.

In some advantageous embodiments, the method comprises providing a third trained artificial neural network configured as an autoencoder or a variational autoencoder, which may also be implemented by the computing device 1100. Preferably, the third trained artificial neural network is trained by unsupervised training with at least 3-dimensional medical images (i.e. with 3-dimensional medical images and/or 4-dimensional medical images). During training, i.e. in the training stage, the third trained artificial neural network "learns" how to compress a provided n-dimensional medical image into la latent representation (usually having fewer features than an input vector of the third trained artificial neural network) and then reconstruct—as accurately as possible—the originally provided n-dimensional medical image from the latent representation.

In the inference stage, the third trained artificial neural network is then unable to compress and or reconstruct novelties and/or anomalies which were not or only rarely included in the training data. Voxel-wise difference (or any other suitable difference metric) between the input and the output of the third trained artificial neural network may be then used as the "novelty score" indicating how "novel" every voxel of the medical image data is compared to the data that was used during training of the third trained artificial neural network.

If the third trained artificial neural network was trained on the same training data as the first trained artificial neural network 300, then a novelty score can be calculated for the provided first medical image 20 in general and/or specifically for each of the at least one segmented structure (or portion) by calculating a novelty score for a region comprising the respective at least one structure. The inverse of this novelty score can be used to determine a confidence score of a label or segmentation. A threshold for this confidence score, indicating whether the label or segmentation should be reviewed by the user, can be learned from a validation data set. Instead of a threshold for the confidence score, a threshold for the novelty score may be determined and used. The validation data set may be a sub-set of the training data set.

The regions of the first (or the second) n-dimensional image 20, 12 corresponding to segmented structures (or portions) for which the corresponding third trained artificial neural network has produced an output that has led to a low quality confidence score being calculated for the region (or, in other words: the regions with confidence scores below the corresponding threshold) may be automatically replaced in the first (or the second) n-dimensional medical image (e.g. by replacing those regions with the corresponding output of the third trained artificial neural network). Such n-dimensional images with replaced regions may be used as input for the at least one first trained artificial neural network.

Another application for autoencoders or variational autoencoders, which may be employed alternatively or additionally to the at least one third trained artificial neural network as described above, may be training an autoencoder or variational autoencoder in unsupervised training on data without any implants and/or anomalies (or without any implants and/or anomalies which shall later be detected based on the autoencoder or variational autoencoder during its inference stage). Possible implants include a pacemaker, an artificial valve and/or the like. An anomaly in the present context may be a tumor, a change in physiological anatomy (e.g. an Aneurysmal Aorta), a deformation (e.g. of a heart valve), a calcification in the cardio-vascular system and/or the like.

Such autoencoders may be applied either to the first n-dimensional medical image 20 (or to an image on which the first n-dimensional medical image 20 is based (e.g. the second n-dimensional medical image 12 as described in the foregoing and/or at least one original medical image 10).

Again, each autoencoder may provide a novelty score indicating regions of the received input which are different and/or unknown from the training data. Optionally, as above, a corresponding novelty score threshold value may be provided or learned and the resulting novelty score of each autoencoder may be compared to the corresponding novelty score threshold value. In this way, an anomaly or an implant may be automatically detected by comparing the produced novelty score to the corresponding novelty score threshold value and segmentations for an anomaly or an implant may be provided, as part of the medical image segmentation and/or separately.

In some embodiments or variations of embodiments, instead of a single first trained artificial neural network 300, an ensemble (i.e. a plurality) of first trained artificial neural networks 300 can be employed. Similarly, instead of the second trained artificial neural network 140, an ensemble (i.e. a plurality) of second trained artificial neural networks 140 can be employed.

For example, the same (at least) part of the provided first n-dimensional medical image may be processed by each of the first trained artificial neural networks 300 of the ensemble in order to generate a respective candidate segmentation.

The individual first trained artificial neural networks 300 are designed and/or trained such that each of them differs from all of the others in at least one way.

As an option, some (e.g. at least one, or all) of the individual first trained artificial neural networks 300 may be trained in different ways, e.g. using different algorithms and/or different formulae and/or different initialisation of the network weights. For example, a different loss function (or:

cost function), or a different optimizer (e.g. ADAM optimizer) may be used for at least some of the individual first trained artificial neural networks 300.

As another option, some (e.g. at least one, or all) of the individual first trained artificial neural networks 300 may be configured with different architectures. Preferably, all of the individual first trained artificial neural networks 300 are configured as a convolutional processing network with U-net architecture, respectively, although some, or even all, of the individual first trained artificial neural networks 300 may also be implemented with different architectures. Any or all of the individual first trained artificial neural networks 300, in particular those that have a U-net architecture, may differ in any or all of the following features:

a number of up-sampling blocks;
a number of down-sampling blocks;
a type and/or a number of layers, of a processing block;
a number of processing blocks;
an element (e.g. a block) of the individual first trained artificial neural network 300 that generates a latent representation or at least one hidden feature in a first instance of the individual first trained artificial neural network 300 that is then used in a second instance of the same individual first trained artificial neural network 300;
and/or the like.

Additionally or alternatively, re-scaling operations could be performed using different algorithms, and/or different target resolutions and/or different not malizations of heart sizes, in some of the individual first trained artificial neural networks 300.

Different architectures of the individual first trained artificial neural networks 300 may be differently suited for different kinds of input images and/or different kind of structures of interest.

The generated candidate segmentations may then be used to generate a result segmentation of the plurality of first trained artificial neural networks 300. For example, the result segmentation may be generated by calculating an average (e.g. mean) of the candidate segmentations. For example, when one pixel, or voxel, of the provided first n-dimensional medical image is determined to be part of a structure (e.g. a heart chamber) with a certainty of 30% by one of the first trained artificial neural networks 300, and the same pixel, or voxel, is determined to be part of the same structure with a certainty of 80% by another one of the first trained artificial neural networks 300, then an averaging of the two results may give a (30%+80%)/2=55% certainty that said pixel, or voxel, is part of that structure. Again, all options described herein for the at least one first trained artificial neural network 300 may be equally applied to, or combined with, the at least one second trained artificial neural network 140.

In an advantageous refinement, the generated candidate segmentations may be used to also estimate a standard deviation of the result segmentation. For example, for at least one of the pixels or voxels of the provided first n-dimensional medical image, the standard deviation may be estimated as root average square of the differences between the values of the average of the candidate segmentations and the individual candidate segmentations generated by the plurality of first trained artificial neural networks 300 for this pixel or voxel. For this pixel or voxel, the result segmentation may be generated by sampling from the Normal distribution with estimated mean and standard deviation and/or the like. The estimated standard deviation may indicate an inverse quality confidence score of the generated result segmentation.

Figure 8:
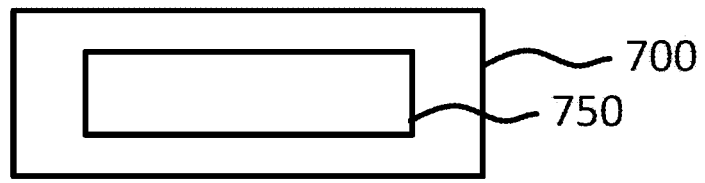
FIG. 8 shows a schematic block diagram illustrating a non-transitory computer-readable data storage medium according to the third aspect of the invention.

FIG. 8 shows a schematic block diagram illustrating a non-transitory computer-readable data storage medium 700 according to the third aspect of the invention. The data storage medium 700 comprises executable program code 750 configured to, when executed, perform the method according to the first aspect. The data storage medium 700 may consist of, or comprise, a CD-ROM, a memory stick, a USB stick, a hard drive, a solid-state data storage device, a DVD, a BluRay-disc, and/or the like.

Figure 9:
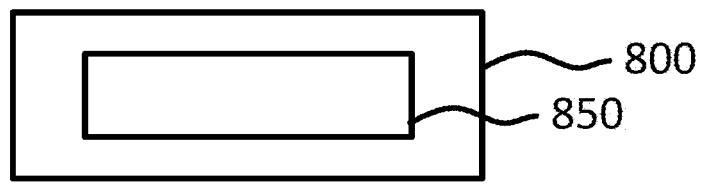
FIG. 9 shows a schematic block diagram illustrating computer program product according to the fourth aspect of the invention.

FIG. 9 shows a schematic block diagram illustrating computer program product 800 according to the fourth aspect of the invention. The computer program product 800 comprises executable program code 850 configured to, when executed, perform the method according to the first aspect.

In the following, examples for the efficacy of the method according to the present invention will be described with respect to FIG. 10A through FIG. 13.

Figure 10A:
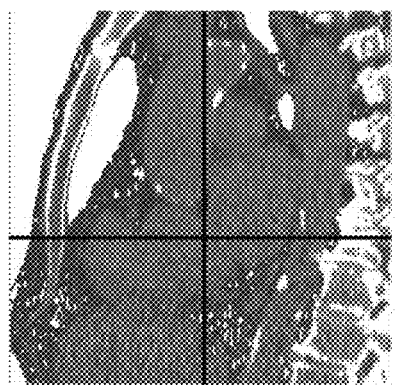
FIGS. 10A, 11A and 12A show exemplary CT scan images of a human heart without contrast agent.
Figure 11A:
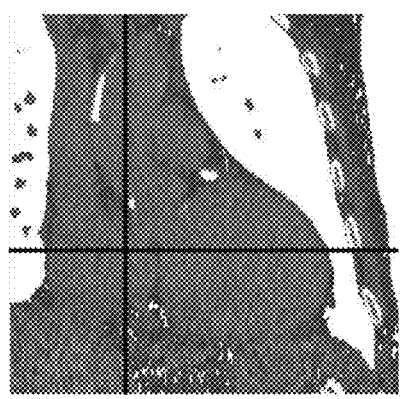
Figure 12A:
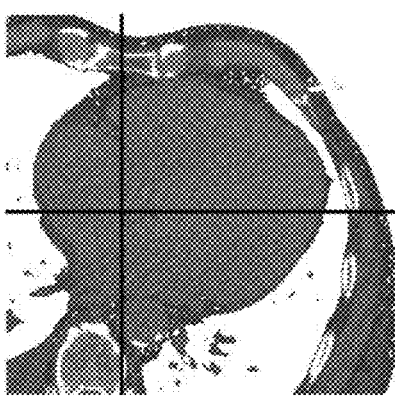

FIGS. 10A, 11A and 12A illustrate exemplary actual CT scan images, without contrast agent, of a human heart. Each of said figures shows a cross-sectional slice. The two perpendicular black lines in each of the figures denote the cross-sectional planes in which the cross-sectional slices of the respective other two figures are arranged. FIG. 10A shows a sagittal view, FIG. 11A a coronal view and FIG. 12A an axial view.

Figure 10B:
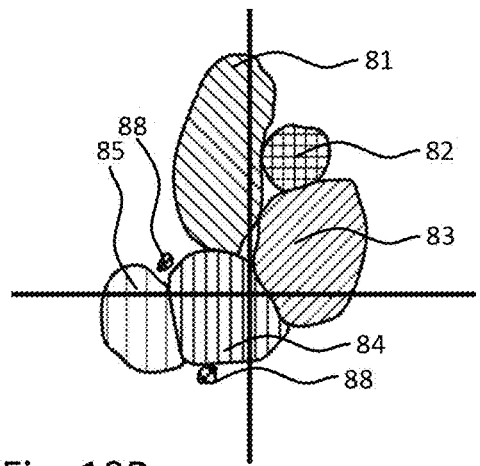
FIGS. 10B, 11B and 12B illustrate actual segmentation results corresponding to the images of FIG. 10A, FIGS. 11A and 1 FIG. 12A, respectively.
Figure 11B:
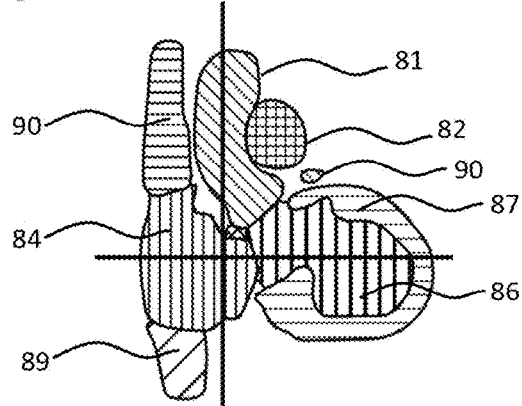
Figure 12B:
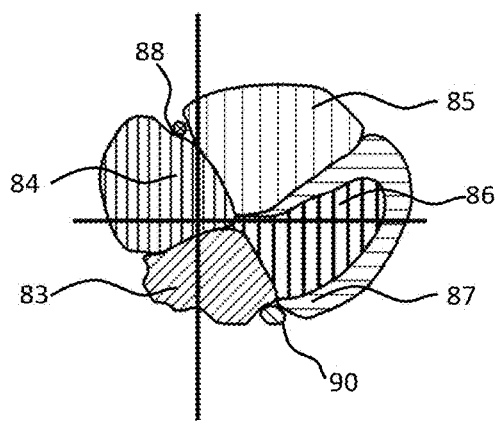

FIGS. 10B, 11B and 12B illustrate a 3-dimensional medical image segmentation according to actual segmentation results, visualized by cross-sectional slices corresponding to the images of FIG. 10A, FIGS. 11A and 1 FIG. 12A, respectively, illustrating the power of the method according to the present invention. In the present example, the following structures of the human heart have been identified by segmentation labels: the Aorta 81, the Pulmonary Artery 82, the Left Atrium 83, the Right Atrium 84, the Right Ventricle 85, the Left Ventricle 86, the Myocardium 87 of the Left Ventricle 86, the Right Coronary Artery 88, the Inferior Vena Cava 89, and the Coronary Sinus 90.

Figure 13:
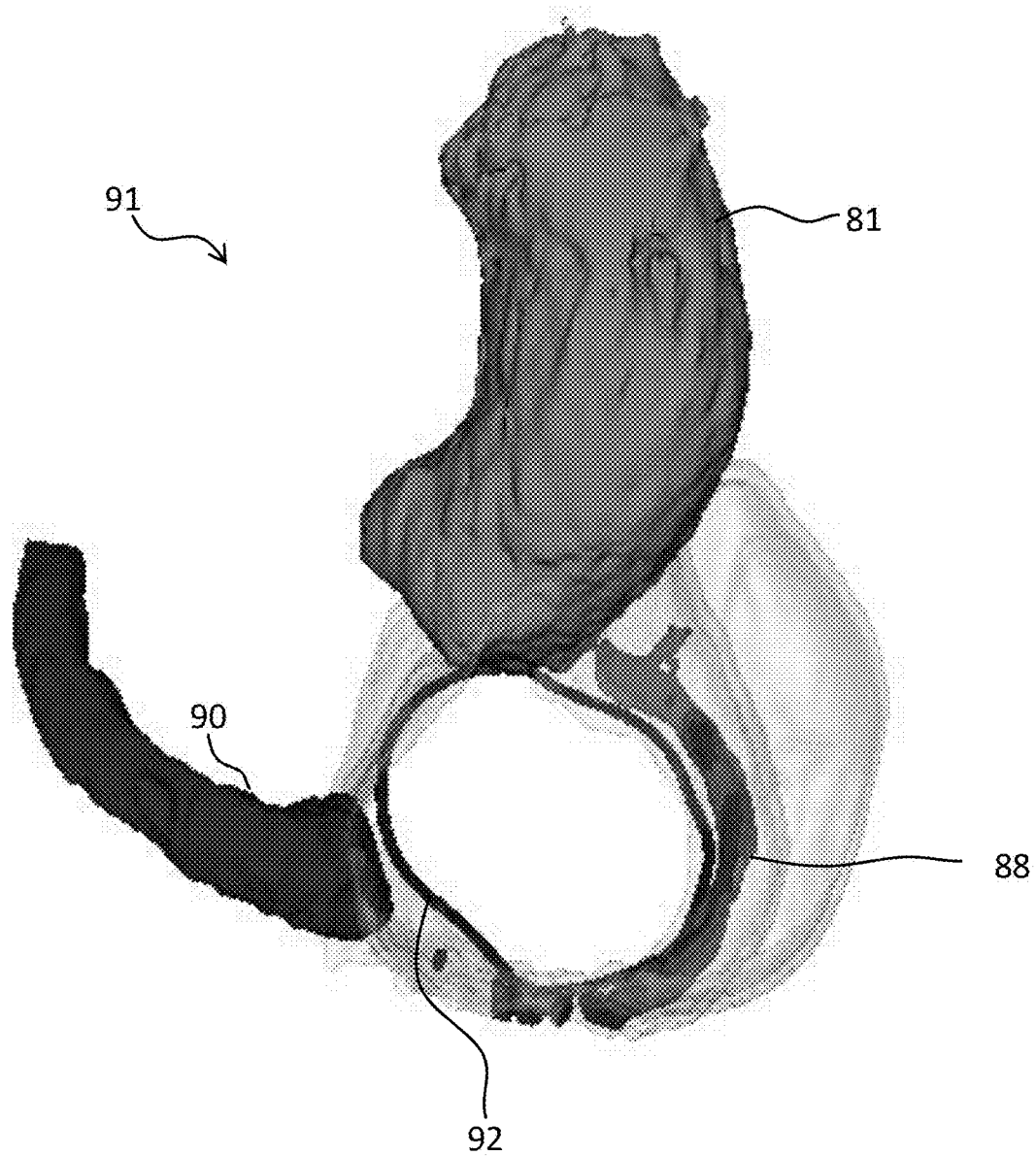
FIG. 13 shows a 3-dimensional representation of segmentation results including the results of FIG. 10B, FIG. 11B and FIG. 12B.

FIG. 13 shows a 3-dimensional representation 91 of a 3-dimensional medical image segmentation including the results of FIG. 10B, FIG. 11B and FIG. 12B. It will be understood that in general a plurality of cross-sectional slices as shown in FIG. 10B, 11B and/or 12B are needed for generating the 3-dimensional representation 91. In FIG. 13, also an annulus structure 92 (or: annulus) of the tricuspid valve is shown which may be generated e.g. by another trained artificial neural network based on the generated 3-dimensional medical image segmentation and/or by another type of algorithm based on the generated labels for the right atrium and the right ventricle, respectively, of the heart.

In the foregoing detailed description, various features are grouped together in one or more examples or examples with the purpose of streamlining the disclosure. It is to be understood that the above description is intended to be illustrative, and not restrictive. It is intended to cover all alternatives, modifications and equivalents. Many other examples will be apparent to one skilled in the art upon reviewing the above specification.

The embodiments were chosen and described in order to best explain the principles of the invention and its practical applications, to thereby enable others skilled in the art to best utilize the invention and various embodiments with various modifications as are suited to the particular use contemplated. In the appended claims and throughout the specification, the terms "including" and "in which" are used as the plain-English equivalents of the respective terms "comprising" and "wherein," respectively. Furthermore, "a" or "one" does not exclude a plurality in the present case.

The invention may be briefly described as follows: the present invention provides a system and a computer-implemented method for generating at least one at least 3-dimensional medical image segmentation for at least one structure of an internal organ, wherein the method comprises the steps of:
   providing a first n-dimensional medical image comprising the at least one structure of the internal organ, wherein n=3 or n=4;
   generating a segmentation of at least part of the provided first n-dimensional medical image using at least one first trained artificial neural network, wherein the at least one first trained artificial neural network is configured as a convolutional processing network with U-net architecture; and
   generating at least one at least 3-dimensional medical image segmentation for the at least one structure of the internal organ based at least on the segmentation generated by the at least one first trained artificial neural network.

The invention claimed is:

1. A computer-implemented method for generating a 4-dimensional medical image segmentation for at least one structure of a human heart, comprising the steps of:
   providing a first 4-dimensional medical image comprising the at least one structure of the human heart, the medical image being based on a computed tomography scan image;
   generating a segmentation of at least part of the provided first 4-dimensional medical image using at least one first trained artificial neural network, wherein the at least one first trained artificial neural network is configured as a convolutional processing network with U-net architecture, wherein each convolutional processing network with U-net architecture comprises:
   a down-sampling path comprising at least two processing convolutional blocks and at least two down-sampling blocks;
   an up-sampling path comprising at least two processing convolutional blocks and at least two up-sampling blocks;
   wherein the down-sampling path generates a direct input and/or an indirect input for the up-sampling path;
   generating at least one 4-dimensional medical image segmentation for the at least one structure of the human heart based at least on the segmentation generated by the at least one first trained artificial neural network;
   providing a computed tomography scan image as a second 4-dimensional medical image;
   generating a segmentation for at least part of the second 4-dimensional medical image using a second trained artificial neural network configured as a convolutional processing network with U-net architecture,
   determining a portion of the segmentation for the second 4-dimensional medical image which comprises the at least one structure of the human heart;
   extracting a portion of the provided second 4-dimensional medical image corresponding to the determined portion of the segmentation for the second 4-dimensional medical image; and
   providing the extracted portion as the first 4-dimensional medical image to the at least one first trained artificial neural network.

2. The method of claim 1, wherein the at least one structure comprises at least one valve structure, at least one blood cavity, at least one muscle tissue structure, at least one implant and/or at least one anomaly.

3. The method according to claim 1,
   wherein the first 4-dimensional medical image comprises a plurality of 3-dimensional medical images, each for a different effective time point;
   wherein a respective segmentation for at least two of the plurality of 3-dimensional medical images is independently generated by the at least one first trained artificial neural network; and
   wherein the 4-dimensional medical image segmentation comprises at least two of the independently generated segmentations for the plurality of 3-dimensional medical images.

4. The method according to claim 3, wherein each 3-dimensional medical image of the plurality of 3-dimensional medical images of the first 4-dimensional medical image is generated from a multi-slice computed tomography scan image by generating 3-dimensional voxels taking into account the values of the pixels of slices of the multi-slice medical image as well as distances between the pixels and distances between the slices.

5. The method according to claim 1, further comprising the step of:
   generating a 3-dimensional medical image segmentation corresponding to a first effective time point within the 4-dimensional medical image segmentation to be generated; and
   wherein at least one 3-dimensional medical image segmentation corresponding to at least one second effective time point within the 4-dimensional medical image segmentation to be generated is generated by the at least one first trained artificial neural network based on at least one output and/or at least one latent representation and/or at least one hidden feature generated by the at least one first trained artificial neural network when generating the 3-dimensional medical image segmentation corresponding to the first effective time point.

6. The method of claim 5, wherein the at least one output and/or at least one latent representation and/or at least one hidden feature generated by the at least one first trained artificial neural network when generating the 3-dimensional medical image segmentation corresponding to the first effective time point is used when generating 3-dimensional medical image segmentations for the at least one structure of the human heart for a plurality of other effective time points that are adjacent to the first effective time point.

7. The method according to claim 5, wherein the first and the second effective time point correspond to different stages of a cardiac cycle.

8. The method according to claim 1, wherein at least one processing block in at least one of the trained artificial neural networks comprises a plurality of convolutional filter layers, wherein at least two of the plurality of convolutional filter layers apply different strides.

9. The method according to claim 1, wherein at least one processing block in at least one of the trained artificial neural networks comprises a bottleneck structure in which a r×r×r 3-dimensional convolution layer follows an q×q×q 3-dimensional convolution layer with a reduced number output channels compared to a number of input channels of the at least one processing block, wherein r and q are integers and wherein q is smaller than r.

10. The method according to claim 1, wherein at least one up-sampling block and/or at least one down-sampling block in at least one of the trained artificial neural networks applies a nearest neighbor and/or trilinear interpolation method.

11. The method according to claim 1, further comprising the steps of:
providing a third trained artificial neural network configured as an autoencoder or a variational autoencoder;
inputting the at least part of the provided first 4-dimensional medical image into the third trained artificial neural network; and
outputting, based on an output of the third trained artificial neural network, an output signal indicating a quality confidence score of the segmentation generated by the at least one first trained artificial neural network and/or indicating an anomaly.

12. The method of claim 1,
wherein a plurality of first trained artificial neural networks which are differently configured and/or differently trained is provided;
wherein at least two of the plurality of the first trained artificial neural networks are configured as a respective convolutional processing network with U-net architecture;
wherein a respective candidate segmentation of at least part of the provided first 4-dimensional medical image is generated by each of the plurality of provided first trained artificial neural networks; and
wherein the 4-dimensional medical image segmentation is generated based on the generated candidate segmentations.

13. A non-transitory computer-readable data storage medium comprising executable program code configured to, when executed, perform the method according to claim 1.

14. The method of claim 1, wherein providing the second 4-dimensional medical image comprises receiving the 4-dimensional medical image via an interface from a picture archiving and communication system of a hospital, or directly from a medical computed tomography imaging device.

15. The method of claim 1, wherein the generated 4-dimensional medical image segmentation comprises labels for at least one leaflet of at least one heart valve.

16. The method of claim 1, wherein the first 4-dimensional medical image is based on a computed tomography scan produced with a total dose of less than 50 ml of contrast agent.

17. The method of claim 1, wherein the generated at least one 4-dimensional medical image segmentation for the at least one structure of the human heart is used for planning and/or guidance of transcatheter heart interventions.

18. A system for generating at least one 4-dimensional medical image segmentation for at least one structure of a human heart, comprising:
a computing device including:
an input module configured to receive a first 4-dimensional medical image of the at least one structure of the human heart, the medical image being based on a computed tomography scan image;
a controller configured and operable to implement at least one first trained artificial neural network, wherein the trained artificial neural network is configured as a convolutional processing network with U-net architecture, wherein each convolutional processing network with U-net architecture includes;
a down-sampling path comprising at least two processing convolutional blocks and at least two down-sampling blocks;
an up-sampling path comprising at least two processing convolutional blocks and at least two up-sampling blocks;
wherein the down-sampling path generates a direct input and/or an indirect input for the up-sampling path;
wherein the first trained artificial neural network is trained and configured to generate a segmentation of at least part of the provided first 4-dimensional medical image; and
an output module configured to generate at least one 4-dimensional medical image segmentation based at least on the segmentation generated by the at least one first trained artificial neural network;
wherein the input module is further configured to receive a second 4-dimensional medical image based on a computer tomography scan image;
wherein said controller is further configured an operable to;
generate a segmentation for at least part of the second 4-dimensional medical image using a second trained artificial neural network configured as a convolutional processing network with U-net architecture,
determine a portion of the segmentation for the second 4-dimensional medical image which comprises the at least one structure of the human heart;
extract a portion of the provided second 4-dimensional medical image corresponding to the determined portion of the segmentation for the second 4-dimensional medical image, and
provide the extracted portion as the first 4-dimensional medical image to the at least one first trained artificial neural network.

19. The system of claim 18, wherein the input module is configured as an interface for receiving the 4-dimensional medical image from a picture archiving and communication system of a hospital or directly from a medical computed tomography imaging device.

20. The system of claim 18, wherein the computing device is configured as a cloud computing platform or as a remote server which is operatively remotely connected to a graphical user interface configured to display information to a user and to receive input from the user.

21. The system of claim 20, wherein the graphical user interface is run on a local machine in a hospital environment.

* * * * *